US010829793B2

(12) United States Patent
Arikawa et al.

(10) Patent No.: US 10,829,793 B2
(45) Date of Patent: Nov. 10, 2020

(54) TRANSFORMANT THAT PRODUCES COPOLYMERIZED PHA CONTAINING 3HH UNIT, AND METHOD FOR PRODUCING SAID PHA

(71) Applicant: KANEKA CORPORATION, Osaka (JP)

(72) Inventors: Hisashi Arikawa, Takasago (JP); Keiji Matsumoto, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/256,780

(22) Filed: Jan. 24, 2019

(65) Prior Publication Data

US 2019/0153486 A1 May 23, 2019

Related U.S. Application Data

(63) Continuation-in-part of application No. PCT/JP2017/025531, filed on Jul. 13, 2017.

(30) Foreign Application Priority Data

Jul. 26, 2016 (JP) ................................. 2016-146286

(51) Int. Cl.
| | | |
|---|---|---|
| *C12N 1/20* | (2006.01) | |
| *C12P 7/62* | (2006.01) | |
| *C08G 63/06* | (2006.01) | |
| *C08L 67/04* | (2006.01) | |
| *C12R 1/01* | (2006.01) | |
| *C12N 15/09* | (2006.01) | |

(52) U.S. Cl.
CPC .............. *C12P 7/625* (2013.01); *C08G 63/06* (2013.01); *C08L 67/04* (2013.01); *C12N 1/20* (2013.01); *C12P 7/62* (2013.01); *C12R 1/01* (2013.01); *C12N 15/09* (2013.01); *C12Y 101/01035* (2013.01)

(58) Field of Classification Search
None
See application file for complete search history.

(56) References Cited

U.S. PATENT DOCUMENTS

| | | | | |
|---|---|---|---|---|
| 5,292,860 | A | 3/1994 | Shiotani et al. | |
| 10,072,255 | B2 * | 9/2018 | Arikawa | C12P 7/625 |
| 2002/0173014 | A1 * | 11/2002 | Hiltunen | C12N 9/0006 |
| | | | | 435/135 |
| 2006/0030014 | A1 * | 2/2006 | Zhang | C12P 7/625 |
| | | | | 435/135 |
| 2013/0017583 | A1 * | 1/2013 | Budde | C12N 9/88 |
| | | | | 435/135 |
| 2013/0071892 | A1 | 3/2013 | Fukui et al. | |
| 2014/0073022 | A1 * | 3/2014 | Pfleger | C12P 7/62 |
| | | | | 435/135 |
| 2014/0349353 | A1 * | 11/2014 | Nomura | C12Y 402/01017 |
| | | | | 435/135 |
| 2016/0040197 | A1 * | 2/2016 | Fukui | C08G 63/06 |
| | | | | 435/135 |
| 2017/0218411 | A1 * | 8/2017 | Fukui | C12N 15/09 |
| 2019/0153486 | A1 * | 5/2019 | Arikawa | C08G 63/06 |

FOREIGN PATENT DOCUMENTS

| | | |
|---|---|---|
| EP | 0 052 459 A1 | 5/1982 |
| EP | 0 114 086 A2 | 7/1984 |
| JP | 57-150393 A | 9/1982 |
| JP | 59-220192 A | 12/1984 |
| JP | 5-93049 A | 4/1993 |
| JP | 7-265065 A | 10/1995 |
| JP | 10-108682 A | 4/1998 |
| JP | 2001-340078 A | 12/2001 |
| WO | WO 01/09364 A1 | 2/2001 |
| WO | WO 2011/105379 A1 | 9/2011 |

OTHER PUBLICATIONS

GenBank Accession No. AAF82684.1, published Jul. 13, 2000 (Year: 2000).*
Haddouche et al., "Engineering polyhydroxyalkanoate content and monomer composition in the oleaginous yeast Yarrowia lipolytica by modifying the β-oxidation multifunctional protein", Appl Microbiol Biotechnol (2011) 91:1327-1340.
Sato et al., "Regulation of 3-hydroxyhexanoate composition in PHBH synthesized by recombinant Cupriavidus necator H16 from plant oil by using butyrate as a co-substrate", Journal of Bioscience and Bioengineering, vol. 120, No. 3, 246-251, 2015.
Insomphun et al., "Improved artificial pathway for biosynthesis of poly (3-hydroxybutyrate-co-3-hydroxyhexanoate) with high $C_6$-monomer composition from fructose in Ralstonia eutropha", Metabolic Engineering 27 (2015) 38-45.
Haataja et al., "Peroxisomal multifunctional enzyme type 2 from the fruitfly: dehydrogenase and hydratase act as separate entities, as revealed by structure and kinetics", Biochem J. (2011) 435, 771-781.
Doi et al., "Microbial Synthesis and Characterization of Poly(3-hydroxybutyrate-co-3-hydroxyhexanoate)", Macromolecules 1995, 28, 4822-4828.

(Continued)

*Primary Examiner* — Richard C Ekstrom
(74) *Attorney, Agent, or Firm* — Oblon, McClelland, Maier & Neustadt, L.L.P.

(57) ABSTRACT

Provided are a transformant that produces a copolymerized PHA containing 3HH units in a higher composition proportion; and a method for producing a copolymerized PHA, using this transformant. The transformant is a transformant that produces a copolymerized PHA containing 3HH units, in which a gene encoding an enzyme having trans-2-enoyl-CoA hydratase activity and (R)-3-hydroxyacyl-CoA dehydrogenase activity is introduced into a prokaryotic microorganism having a PHA synthetase gene capable of synthesizing the copolymerized PHA containing the 3HH units. The method is a method for producing a copolymerized PHA containing 3HH units, which includes a step of culturing this transformant.

18 Claims, No Drawings

Specification includes a Sequence Listing.

(56) References Cited

OTHER PUBLICATIONS

Fukui et al., "Cloning and Analysis of the Poly(3-Hydroxybutyrate-co-3-Hydroxyhexanoate) Biosynthesis Genes of Aeromonas caviae", Journal of Bacteriology, vol. 179, No. 15, Aug. 1997, p. 4821-4830.
Kawashima et al., "Characterization and Functional Analyses of R-Specific Enoyl Coenzyme A Hydratases in Polyhydroxyalkanoate-Producing Ralstonia eutropha", Applied and Environmental Microbiology, Jan. 2012, vol. 78, No. 2, p. 493-502.
Fukui et al., "Engineering of Ralstonia eutropha for Production of Poly(3-hydroxybutyrate-co-3-hydroxyhexanoate) from Fructose and Solid-State Properties of the Copolymer", Biomacromolecules, vol. 3, No. 3, 2002, 3, 618-624.

* cited by examiner

TRANSFORMANT THAT PRODUCES COPOLYMERIZED PHA CONTAINING 3HH UNIT, AND METHOD FOR PRODUCING SAID PHA

CROSS-REFERENCE TO RELATED APPLICATIONS

The present application is a continuation-in-part of International Application No. PCT/JP2017/025531, filed Jul. 13, 2017, which is based upon and claims the benefits of priority to Japanese Application No. 2016-146286, filed Jul. 26, 2016. The entire contents of these applications are incorporated herein by reference.

TECHNICAL FIELD

The present invention relates to a transformant that produces a copolymerized PHA containing a 3HH unit, and a method for producing the PHA.

BACKGROUND ART

A polyhydroxyalkanoate (hereinafter referred to also as a PHA) is a polyester type organic polymer produced by various microorganism species. The PHA is a thermoplastic polymer having biodegradability, and can be produced using a renewable source as a raw material. From these matters, trails have been made for producing the PHA industrially as an environment harmony type material or biocompatible material, and making use of the PHA for various industries.

It has been known up to now that many microorganisms accumulate, in their bacterial cell, a PHA as an energy storing material. A typical example of the PHA is poly-3-hydroxybutyric acid (hereinafter referred to also as P(3HB)), which is a homopolymer made from 3-hydroxybutyric acid (referred to also as 3HB). P(3HB) is a thermoplastic polymer, and is biodegraded in a natural environment. Thus, attention is paid to the polymer as an environment-friendly plastic material. However, P(3HB) is high in crystallinity to have a hard and brittle natural, so that a practical application scope thereof is limited. In order to widen the application scope, it is necessary to give softness to P(3HB).

Thus, a development has been made about a copolymerized PHA made from 3HB and 3-hydroxyvaleric acid (hereinafter referred to as 3HV) (hereinafter the PHA will be referred to as P(3HB-co-3HV)), and a producing method therefor (see, for example, PTL 1 and PTL 2). P(3HB-co-3HV) is richer in softness than P(3HB). Thus, it has been conceived that P(3HB-co-3HV) is applicable to various articles. In reality, however, even when the molar fraction of 3HV in P(3HB-co-3HV) is increased, this copolymer is poor in physical-property-change associated with the increase. The softness is not improved up to the degree of being required for working the copolymer, in particular, into a film, a sheet, a soft package container or the like. Consequently, the copolymer is used only to limited fields of shampoo bottles, handgrips of disposable razors, hard shaped bodies, and others.

Furthermore, researches have been made about a copolymerized PHA made from 3HB and 3-hydroxyhexanoic acid (hereinafter referred to also as 3HH) (hereinafter the copolymer will be referred to also P(3HB-co-3HH)) to heighten a PHA in softness, and a producing method therefor (see PTL 3 and PTL 4). In these reports, P(3HB-co-3HH) is produced by using a wild strain of *Aeromonas caviae* that is isolated from soil to ferment a fatty acid, such as oleic acid or palmitic acid, as a carbon source.

Researches have been made also about physical properties of P(3HB-co-3HH) (see NPTL 1). According to this report, a fatty acid having 12 or more carbon atoms is used as only one carbon source to culture *A. caviae* to produce P(3HB-co-3HH) species having various 3HH composition proportions through fermentation. The following have been made evident: as P(3HB-co-3HH) is increased in 3HH composition proportion therein, this copolymer comes to show natures extending from a hard and brittle nature as P(3HB) shows gradually to a softer nature; and as the 3HH composition proportion is more heightened, the copolymer shows a softness higher than that of P(3HB-co-3HV). In other words, by changing P(3HB-co-3HH) in 3HH composition proportion therein, this copolymer can be caused to have such broad physical properties that the copolymer is usable as polymers extending from hard polymers to soft polymers. Thus, this copolymer can be expected to be applied to board fields.

Moreover, examinations have been made about the PHA producing performance of a transformant which has been yielded by using, as a host, *C. necator* and transforming this host with a PHA synthetase expression plasmid, such as pJRDEE32 or pJRDEE32d13, in which, for example, a polyester synthetase gene or R-body specific enoyl-CoA hydratase gene is introduced into a plasmid pJRD215 (ATCC 37533) (see PTL 5, and NPTL 2). After the culturing of this bacterial strain, the microbiomass of the strain is originally as low as 4 g/L. However, the following have been found out: a polymer-producing performance of this strain is improved to give a microbiomass of 45 g/L and a polymer content of 62.5% by improving culturing-conditions for the bacterial strain, using plant oils and fats as carbon sources; and further the 3HH composition proportion therein is improved up to 8.1% by mol by this condition-improvement. As described herein, attempts have been made about improvements of P(3HB-co-3HH) in 3HH proportion therein and in polymer-producing performance (see PTL 6).

A report has been made also about an improvement of such a polymer in 3HH composition proportion therein by incorporating R body specific enoyl-CoA hydratase genes into a chromosome DNA of *C. necator* (see PTL 7 and NPTL 3). According to this report, plural R body specific enoyl-CoA hydratase genes are introduced into a pha operon region containing a pha synthetase gene of *C. necator* to improve the 3HH composition proportion in PHBH, which is produced using plant oils and fats as raw materials, up to 10.5% by mole.

As described above, in many examples, the production of P(3HB-co-3HH) is attained using plant oils and fats as raw materials. Apart from these examples, researches have been made also about the production of P(3HB-co-3HH) from saccharine material (see NPTL 4). According to this report, a crotonyl-CoA reductase gene derived from *Streptomyces cinnamonensis* is introduced into *C. necator* to produce P(3HB-co-3HH) containing a small quantity of 3HH units, using fructose as raw material.

Furthermore, in recent years, a report has been made about an improvement of the 3HH composition proportion in such a polymer by introducing not only the crotonyl-CoA reductase but also ethylmalonyl-CoA decarboxylase gene thereinto (see NPTL 5).

CITATION LISTS

Patent Literatures

PTL 1: JP S57-150393 A
PTL 2: JP S59-220192 A

PTL 3: JP H05-93049 A
PTL 4: JP H07-265065 A
PTL 5: JP H10-108682 A
PTL 6: JP 2001-340078 A
PTL 7: WO 2011/105379

Non Patent Literature

NPTL 1: Y. Doi, S. Kitamura, H. Abe, Macromolecules, 28, pp. 4822-4823 (1995)
NPTL 2: T. Fukui, Y. Doi, J. Bacteriol, 179, 15, pp. 4821-4830 (1997)
NPTL 3: Y. Kawashima et al., Appl. Environ. Microbiol., 78, pp. 493-502 (2012)
NPTL 4: T. Fukui, H. Abe, Y. Doi, Biomacromolecules, 3, pp. 618-624 (2002)
NPTL 5: C. Insomphun, H. Xie, J. Mifune, Y. Kawashima, I. Orita, S. Nakamura, T. Fukui, metabolic engineering, 27, pp. 38-45 (2015)

SUMMARY OF INVENTION

Technical Problem

An object of the present invention is to provide a transformant that produces a copolymerized PHA containing 3HH units in a higher composition proportion; and a method for producing a copolymerized PHA, using this transformant.

Solution to Problem

In order to solve the above-mentioned problems, the inventors have repeated eager researches to find out that a copolymerized PHA containing 3HH units in a higher composition proportion can be produced through fermentation by introducing a gene encoding an enzyme having both of trans-2-enoyl-CoA hydratase activity and (R)-3-hydroxyacyl-CoA dehydrogenase activity, this gene being a gene that prokaryotic microorganisms do not usually have and thus only eukaryotes have, into a prokaryotic microorganism having a PHA synthetase gene capable of synthesizing the copolymerized PHA containing the 3HH units. In this way, the present invention has been accomplished.

Accordingly, the present invention relates to a transformant that produces a copolymerized PHA containing a 3HH unit, in which a gene encoding an enzyme having trans-2-enoyl-CoA hydratase activity and (R)-3-hydroxyacyl-CoA dehydrogenase activity is introduced into a prokaryotic microorganism having a PHA synthetase gene capable of synthesizing the copolymerized PHA containing the 3HH unit.

The transformant is preferably a transformant into which a gene encoding a crotonyl-CoA reductase (CCR) is further introduced. The transformant is more preferably a transformant into which a gene encoding an ethylmalonyl-CoA decarboxylase is further introduced.

The gene encoding the enzyme having trans-2-enoyl-CoA hydratase activity and (R)-3-hydroxyacyl-CoA dehydrogenase activity is preferably a gene derived from *Yarrowia lipolytica*, or a gene derived from *Drosophila melanogaster.*

The prokaryotic microorganism is preferably a bacterium, more preferably a bacterium belonging to a genus of *Cupriavidus*, even more preferably *Cupriavidus necator.*

A second aspect of the present invention is a method for producing a copolymerized PHA containing a 3HH unit, the method including a step of culturing the above-defined transformant. The copolymerized PHA is preferably P(3HB-co-3HH).

Advantageous Effects of Invention

The present invention can provide a transformant that produces a copolymerized PHA containing 3HH units in a higher composition proportion. The invention makes it possible to produce a copolymerized PHA containing 3HH units in a higher composition proportion through fermentation by culturing this transformant.

DESCRIPTION OF EMBODIMENTS

Hereinafter, the present invention will be described in more detail.

1. Transformant That Produces Copolymerized PHA Containing 3HH Units

The present invention provides a transformant that produces a copolymerized PHA containing 3HH units in a higher composition proportion, in which a gene encoding an enzyme having trans-2-enoyl-CoA hydratase activity and (R)-3-hydroxyacyl-CoA dehydrogenase activity is introduced into a prokaryotic microorganism having a PHA synthetase gene capable of synthesizing the copolymerized PHA containing the 3HH units.

In the present invention, the prokaryotic microorganism, which is an original strain to which the gene encoding the above-mentioned enzyme is to be introduced, is not particularly limited as far as the prokaryotic microorganism is a prokaryotic microorganism having a PHA synthetase gene capable of synthesizing a copolymerized PHA containing 3HH units. Such a prokaryotic microorganism may be, as well as a wild strain which originally has the PHA synthetase gene, a variant obtained by subjecting such a wild strain artificially to spontaneous mutation treatment, or a recombinant prokaryotic microorganism strain into which a gene engineering technique is used to introduce a PHA synthetase foreign gene and/or a PHA-production-related enzyme gene.

The wording that "the PHA synthetase gene is capable of synthesizing a copolymerized PHA containing 3HH units" means not only that the gene can synthesize the copolymerized PHA containing the 3HH units under any culturing condition but also that the gene can synthesize the copolymerized PHA containing the 3HH units under a specified culturing condition. For example, a bacterial strain described in Comparative Example 2, which will be described later, does not synthesize any copolymerized PHA containing 3HH units under a culturing condition that glucose is used as a single carbon source. However, this bacterial strain can synthesize a copolymerized PHA containing 3HH units under a culturing condition that an oil and fat is contained as a carbon source. Thus, this bacterial strain falls under "prokaryotic microorganisms each having a PHA synthetase gene capable of synthesizing a copolymerized PHA containing 3HH units".

Specific examples of such a prokaryotic microorganism include bacteria, actinomycetes, cyanobacteria and archaebacteria. The prokaryotic microorganism is preferably a bacterium. Preferred examples of the bacterium include bacterial belonging to the genus *Ralstonia*, the genus *Cupriavidus*, the genus *Wautersia*, the genus *Aeromonas*, the genus *Escherichia*, the genus *Alcaligenes*, and the genus *Pseudomonas*. From the viewpoint of safety, and the producing performance, more preferred are bacteria belonging to the genus *Ralstonia*, the genus *Cupriavidus*, the genus

*Aeromonas*, and the genus *Wautersia*, even more preferred are bacteria belonging to the genus *Cupriavidus* or the genus *Aeromonas*, and even more preferred are bacteria belonging to the genus *Cupriavidus*. Particularly preferred is *Cupriavidus necator*.

When the prokaryotic microorganism having a PHA synthetase gene capable of synthesizing a copolymerized PHA containing 3HH units is a recombinant prokaryotic microorganism strain into which a gene engineering technique is used to introduce a PHA synthetase foreign gene, the PHA synthetase foreign gene is not particularly limited as far as the gene is a gene having a function of taking in 3HH and producing a copolymerized PHA containing 3HH units. Examples of such a PHA synthetase gene include a PHA synthetase gene derived from *Aeromonas caviae* and encoding an enzyme having an amino acid sequence described in SEQ IS NO: 1, or a PHA synthetase gene encoding a polypeptide having a sequence homology of 85% or more to the amino acid sequence and further having activity of synthesizing a copolymerized PHA containing 3HH unit. However, the PHA synthetase gene is not limited to these genes. The sequence homology is preferably 90% or more, more preferably 95% or more, and particularly preferably 99% or more. Out of these examples, preferred is a PHA synthetase gene which can synthesize P(3HB-co-3HH) as the copolymerized PHA containing 3HH unit; and more preferred is, for example, a PHA synthetase gene encoding a PHA synthetase having an amino acid sequence described in SEQ ID NO: 2.

In the present invention, the prokaryotic microorganism, which is an original strain, is most preferably a recombinant prokaryotic microorganism strain in which a PHA synthetase gene derived from *Aeromonas caviae* is introduced into *Cupriavidus necator*.

In the present invention, the following gene is introduced into the prokaryotic microorganism: a gene encoding an enzyme having trans-2-enoyl-CoA hydratase activity and (R)-3-hydroxyacyl-CoA dehydrogenase activity (hereinafter this gene may be abbreviated to a transgene).

This transgene is a gene which prokaryotic organisms do not usually have, and which is derived from a eukaryote. Accordingly, in the present invention, a gene derived from a eukaryote is introduced into a prokaryotic microorganism. A transformant obtained by introducing the transgene into a prokaryotic microorganism having the PHA synthetase gene becomes possible to produce a copolymerized PHA containing 3HH units in a higher composition proportion.

Usually, β oxidation inside a prokaryotic microorganism is a reaction passing through trans-2-enoyl-CoA to (S)-3-hydroxyacyl-CoA. Through the route of this β oxidation, a 3HH of an R body, from which copolymerized PHA containing 3HH unit is made, is not produced. However, according to the present invention, the introduction of the transgene into a prokaryotic microorganism attains a construction of a metabolic route passing through trans-2-enoyl-CoA to (R)-3-hydroxyacyl-CoA when an oil and fat is used as a carbon source. Through this route, (R)-3-hydroxyacyl-CoA, which has 6 carbon numbers, comes to be synthesized. Consequently, a 3HH monomer of an R body is produced to heighten the composition proportion of 3HH units in a copolymerized PHA as the final synthesized product. Such a matter is presumed.

In the meantime, when the production of a copolymerized PHA containing 3HH unit is attempted in a culture using saccharide as a carbon source, it would be necessary to synthesize acetyl-CoA, which has 2 carbon atoms, into (R)-3-hydroxyacyl-CoA, which has 6 carbon atoms, by a reaction the direction of which is reverse to that of ordinary β oxidation. Also in this case, the introduction of the transgene into a prokaryotic microorganism attains a construction of a metabolic route passing through (R)-3-hydroxyacyl-CoA, so that a 3HH monomer of an R body is effectively produced to heighten the composition proportion of 3HH units in a copolymerized PHA as the final synthesized product. Such a matter is presumed.

The transgene is not particularly limited as far as the gene is a gene encoding an enzyme having trans-2-enoyl-CoA hydratase activity and (R)-3-hydroxyacyl-CoA dehydrogenase activity. The gene is usually a gene known as an MFE2 gene encoding a multifunctional enzyme type 2 (MFE-2). Specific examples thereof include an MFE2 gene derived from *Yarrowia lipolytica* (the so-called an MFE-1 gene), an MFE2 gene derived from, for example, *Drosophila melanogaster*, and an MFE2 gene derived from *Saccharomyces cerevisiae* (the so-called a FOX2 gene).

The transgene is a gene derived from a eukaryote; thus, the gene may contain an untranslated region that is generally called an intron. In such a case, a transgene in a state that a base sequence corresponding to an intron is removed from an original gene thereof may be introduced into a prokaryotic microorganism. Moreover, a codon in the transgene may be appropriately modified in accordance with the host.

The transgene is preferably an MFE2 gene encoding MFE-2. Specific examples thereof include an MFE2 gene derived from *Yarrowia lipolytica* and encoding an amino acid sequence described in SEQ ID NO: 3; an MFE2 gene derived from *Drosophila melanogaster* and encoding an amino acid sequence described in SEQ ID NO: 4; and a gene encoding a polypeptide having a homology of 90% or more to any one of these amino acid sequences and further showing trans-2-enoyl-CoA hydratase activity and (R)-3-hydroxyacyl-CoA dehydrogenase activity. The sequence homology is preferably 95% or more, more preferably 97% or more, and particularly preferably 99% or more.

NPTL 5 reports that P(3HB-co-3HH) can be produced using a saccharide as a carbon source by introducing a crotonyl-CoA reductase (CCR) gene and an ethylmalonyl-CoA decarboxylase (EMD) gene into *Cupriavidus necator* into which a PHA synthetase gene which can take in a 3-HH monomer is introduced. Also about the transformant of the present invention, a CCR gene and/or an EMD gene, as well as the transgene, may be introduced thereinto. When a saccharide is used as a carbon source, the introduction of the CCR gene and/or EMD gene makes it possible to enhance the synthesis route of (R)-3-hydroxyacyl-CoA, which has 6 carbon atoms, or make the route the efficient. Thus, in the produced copolymerized PHA, the composition proportion of 3HH units can be improved.

In the description of the present application, CCR is an enzyme which reduces a crotonyl-CoA, which has 4 carbon atoms and is an intermediate in a fatty acid beta-oxidation route, to produce butyryl-CoA. The derivation of the CCR gene usable in the present invention is not particularly limited as long as the reductase after the gene is translated has the above-mentioned crotonyl-CoA reductase activity. Examples thereof include a gene encoding a crotonyl-CoA reductase derived from *S. cinnamonensis* (Gene Bank Accession No. AF178673), and a gene encoding a crotonyl-CoA reductase derived from a methanol assimilating bacterium *M. extorquen* (NCBI-Gene ID: 7990208). Preferred examples thereof include a gene encoding a crotonyl-CoA reductase having an amino acid sequence described in SEQ ID NO: 5, and a gene encoding a polypeptide which has a sequence homology of 90% or more to this amino acid sequence and which has crotonyl-CoA reductase activity.

In the description of the present application, the EMD is an enzyme which catalyzes a decarboxylation reaction of ethylmalonyl-CoA, which is generated by a side reaction by aid of, e.g., the crotonyl-CoA reductase or propionyl-CoA carboxylase, to butyryl-CoA. The derivation of the EMD is not particularly limited as long as this enzyme has this activity. The enzyme is, for example, an ethylmalonyl-CoA decarboxylase derived from a mouse and having an amino acid sequence described in SEQ ID NO: 6. A gene base sequence which encodes this amino acid sequence is, for example, a base sequence described in SEQ ID NO: 7. However, the gene base sequence is not limited to this base sequence.

When the prokaryotic microorganism into which the transgene is introduced has a low glucose assimilability or no glucose assimilability, glucose assimilability can be given to the transformant of the present invention or the glucose assimilability of the transformant can be enhanced by, for example, a method of gene mutation, gene disruption, the enhancement of gene expression, or foreign gene introduction. For example, a C. necator H16 strain has no gene of a glucose-taking-in type. Thus, the strain cannot assimilate glucose. The method for giving glucose assimilability to the C. necator H16 strain is not particularly limited. An example thereof is a method of substituting G which is the 793$^{rd}$ base in nagE, which is a gene for taking in N-acetyl glucosamine, with C; and further disrupting nagR, which is a gene encoding a transcriptional regulator, to give glucose assimilability thereto (Journal of Bioscience and Bioengineering, vol. 113, 63 (2012)). Moreover, another example thereof is a method of introducing a foreign gene encoding a glucose transporter into the strain to give glucose assimilability thereto (JP 2009-225662 A). Furthermore, a method of introducing a glucose-phosphorylation enzyme gene into the strain may be useful.

In the transformant of the present invention, the introduced transgene or any other introduced gene may be present on a DNA of, for example, a chromosome, a plasmid or a megaplasmid which the prokaryotic microorganism that is a host has; or may be present on a DNA introduced artificially into the transformant, for example, on a plasmid vector or an artificial chromosome. However, from the viewpoint of the retention of the introduced gene, this gene is preferably present on a chromosome or a megaplasmid which the prokaryotic microorganism has; and is more preferably present on a chromosome which the prokaryotic microorganism has. When the microorganism, which is a host, originally has such a gene, the expression level of the gene may be increased by, for example, the substitution, deletion or addition of a base sequence, instead of the introduction, this base sequence being present at the upstream side of the gene which the prokaryotic microorganism originally has.

A method for applying a moiety-specific substitution or insertion of any DNA onto a DNA which a microorganism has is well known for those skilled in the art, and the method is usable when the transformant of the present invention is produced. The method is not particularly limited, and examples thereof include a method using a mechanism of transposon and homologous recombination (Ohman et al., J. Bacteriol., vol. 162, p. 1068 (1985)); a method using, as a principle, moiety-specific introduction caused by a homologous recombination mechanism, and dropout based on homologous recombination at the second stage (Noti et al., Methods Enzymol., vol. 154, p. 197 (1987)); and a method of causing a sacB gene derived from *Bacillus subtilis* to coexist, and then easily isolating, as a sucrose-added-medium resistant strain, a microorganism strain in which the gene is dropped out by homologous recombination at a second stage of this method (Schweizer, Mol. Microbiol., vol. 6, p. 1195 (1992), and Lenz et al., J. Bacteriol., vol. 176, p. 4385 (1994)). The method for introducing a vector into a cell is not particularly limited, either. Examples thereof include a calcium chloride method, an electroporation method, a polyethylene glycol method, and a spheroplast method.

About gene cloning and gene recombination techniques, techniques described in the following are usable: for example, Sambrook, J. et al., Molecular Cloning, A Laboratory Manual, Cold Spring Harbor Laboratory Press (1989 or 2001).

The promoter for expressing each of the above-mentioned various genes is not particularly limited. For example, the following is usable: a promoter of a phaC1 gene or a promoter of a phaP1 gene of *Cupriavidus necator*; a lac promoter, a lacUV5 promoter, a trc promoter, a tic promoter or a tac promoter derived from *Escherichia coli*; or a Poe1 promoter that has a base sequence described in SEQ ID NO: 8 and is artificially produced.

2. Method for Producing PHA

The transformant of the present invention is cultured, thereby making it possible to produce a PHA. By collecting the resultant PHA, the production of the PHA can be attained.

In the PHA production according to the present invention, the transformant is preferably cultured in a medium containing a carbon source, and nutrition sources other than the carbon source, for example, a nitrogen source, inorganic salts, and other organic nutrition sources.

As the carbon source, any carbon source is usable as long as the transformant of the present invention can assimilate the source. Preferred examples thereof include saccharides such as glucose, fructose and sucrose; oils and fats such as palm oil, palm kernel oil, corn oil, coconut oil, olive oil, soybean oil, linseed oil, and Jatropha oil, and fractionized oils thereof; aliphatic acids such as lauric acid, oleic acid, stearic acid, palmitic acid and myristic acid, and derivatives thereof; gases such as carbon dioxide, carbon monoxide and methane; and alcohols such as methanol and ethanol.

Examples of the nitrogen source include ammonia; ammonium slats such as ammonium chloride, ammonium sulfate, and ammonium phosphate; and peptone, meat extracts, and yeast extracts. Examples of the inorganic salts include potassium dihydrogenphosphate, sodium dihydrogenphosphate, magnesium phosphate, magnesium sulfate, and sodium chloride. Examples of the other organic nutrition sources include amino acids such as glycine, alanine, serine, threonine, and proline; and vitamins such as vitamin B1, vitamin B12, and vitamin C.

When the transformant of the present invention is cultured, the culturing temperature, the culturing period, the pH in the culturing, the medium, and other conditions may be conditions used ordinarily used to culture a prokaryotic microorganism, which is a host, examples of this microorganism including bacteria in the genus *Ralstonia*, the genus *Cupriavidus*, the genus *Wautersia*, the genus *Aeromonas*, the genus *Escherichia*, the genus *Alcaligenes*, the genus *Pseudomonas*, and others.

The species of the PHA produced in the present invention is not particularly limited as far as the PHA is a copolymerized PHA containing 3HH units. The PHA is preferably a copolymerized PHA yielded by polymerizing one or more monomers selected from 2-hydroxyalkanoic acids each having 4 to 16 carbon atoms, 3-hydroxyalkanoic acids (except 3HH) and 4-hydroxyalkanoic acids, and 3HH; and is more preferably P(3HB-co-3HH), which is a copolymer made from 3-hydroxybutyric acid and 3-hydroxyhexanoic acid. The species of the produced PHA is appropriately selectable in accordance with the species of a PHA synthetase gene which the used prokaryotic microorganism has or which is separately introduced, the species of genes of a metabolic system related to the synthesis, the culturing conditions, and others, correspondingly to a purpose of the PHA.

After the transformant is cultured in the present invention, the collection of the PHA from the bacterial cells is not particularly limited, and can be attained by, for example, the following method. After the end of the culturing, for example, a centrifugal separator is used to separate the bacterial cells from the cultured liquid. The bacterial cells are washed with, for example, distillated water or methanol, and dried. From the dried bacterial cells, an organic solvent such as chloroform is used to extract the PHA. Form this PHA-containing solution in the organic solvent, bacterial cell components are removed by, for example, filtration. A poor solvent such as methanol or hexane is added to the filtrate to precipitate the PHA. Furthermore, filtration or centrifugal separation is used to remove the supernatant. The remnant is then dried to collect the PHA.

The weight-average molecular weight (Mw) of the resultant PHA, and the composition of 3HH and other monomers (% by moles) therein can be analyzed by, for example, gel permeation chromatography, a gas chromatographic method or a nuclear magnetic resonance method.

EXAMPLES

Hereinafter, the present invention will be described in detail by way of working examples thereof. However, the invention is not limited by these examples. General genetic manipulations can be performed as described in Molecular Cloning (Cold Spring Harbor Laboratory Press (1989)). Any enzyme, any cloning host, and any other that are used in the genetic manipulations are commercially available from suppliers in the market, and are usable in accordance with their manual. The enzyme is not particularly limited as long as the enzyme is an enzyme usable for genetic manipulation.

Any KNK005 strain used in production examples, the working examples, and comparative examples described below is a transformant in which a PHA synthetase gene (gene encoding a PHA synthetase having an amino acid sequence described in SEQ ID NO: 2) derived from *Aeromonas caviae* is introduced onto a chromosome of a *C. necator* H16 strain. Any KNK005ΔphaZ1,2,6 strain is a transformant of KNK005 strain, in which a phaZ1,2,6 gene is deleted on a chromosome of a *C. necator* H16 strain. These transformants can be produced in accordance with methods described in a specification of U.S. Pat. No. 7,384,766, and WO 2014/065253.

(Production Example 1) Production of Plasmid for MFE2yl Plasmid Expression

In this production example, a plasmid for MFE2yl expression was produced. The production was performed as follows:

By PCR using a synthesized oligo DNA, a DNA fragment (SEQ ID NO: 9) was yielded which had an MFE2 (MFE2yl) gene sequence derived from *Yarrowia lipolytica*. This DNA fragment was digested with restriction enzymes MunI and SpeI. The resultant DNA fragment was linked to a product in which a plasmid vector pCUP2 described in WO 2007/049716 was cut with MunI and SpeI, so as to yield a plasmid vector pCUP2-MFE2yl.

Furthermore, by PCR using a synthesized oligo DNA, a DNA fragment (SEQ ID NO: 10) was yielded which had a trc promoter. This DNA fragment was digested with restriction enzymes EcoRI and MunI. The resultant DNA fragment was linked to a product in which the plasmid vector pCUP2-MFE2yl was cut with MunI. From the resultant plasmid vectors, the following was selected: a plasmid vector in which the sequence of the trc promoter was linked to the sequence of MFE2yl in a direction along which the MFE2yl sequence was positioned at the downstream side of the trc promoter sequence. The selected vector was used as a plasmid vector pCUP2-trc-MFE2yl.

(Example 1) Production of pCUP2-trc-MFE2yl/KNK005 Strain

In this example, the plasmid vector pCUP2-trc-MFE2yl yielded in Production Example 1 was introduced into a KNK005 strain to yield a transformant pCUP2-trc-MFE2yl/KNK005 strain.

The introduction of the plasmid vector into the cells was attained by electrical introduction as follows: A used gene introducing device was a gene pulser manufactured by Bio-Rad Laboratories, Inc., and a used cuvette was a cuvette having a gap of 0.2 cm and manufactured by the same incorporated company Bio-Rad Laboratories. Into the cuvette were injected 400 µL, of the competent cells and 20 µL of the expression vector, and then the cuvette was set to the pulsing device to apply electric pulses thereto under conditions of an electrostatic capacitance of 25 µF, a voltage of 1.5 kV, and a resistance value of 800Ω. After the pulsing, the bacterial liquid in the cuvette was shaken and cultured on a nutrient broth medium (manufactured by a company Difco) at 30° C. for 3 hours. The bacterial liquid was cultured on a selection plate (nutrient agar medium (manufactured by the company Difco), using kanamycin (100 mg/L) at 30° C. for 2 days to gain a growing transformant pCUP2-trc-MFE2yl/KNK005 strain.

(Production Example 2) Production of KNK005ΔphaZ1,2,6/nagEG793C,dR/Z2,Z6::Poe1-ccr-emd Strain Initially, a plasmid for chromosome-substitution was produced. The production was performed as follows:

By PCR using a synthesized oligo DNA, a DNA fragment (SEQ ID NO: 11) was yielded which contained a partial sequence of a nagE gene. The resultant DNA fragment was digested with a restriction enzyme SwaI. This DNA fragment was linked to a vector pNS2X-sacB digested with SwaI in the same way and described in JP 2007-259708 A through a DNA ligase (Ligation High (manufactured by Toyobo Co., Ltd.)) to produce a plasmid vector pNS2X-sacB+nagEG793C, for chromosome-substitution, having base sequences on the upstream side and the downstream side of the 793$^{th}$ base of the nagE structural gene, and further containing a base sequence in which the base G at the 793$^{th}$ base of the nagE structural gene was substituted with C.

Next, the plasmid vector pNS2X-sacB+nagEG793C for chromosome-substitution was used to produce a chromosome substituted strain KNK005ΔphaZ1,2,6/nagEG793C as described hereinafter.

The plasmid vector pNS2X-sacB+nagEG793C for chromosome-substitution was used to transform an *E. coli* S17-1 strain (ATCC47055). The resultant transformant and a KNK005ΔphaZ1,2,6 strain were subjected to mixed culturing on a nutrient agar medium (manufactured by the company Difco) to attain a conjugative transfer.

The resultant cultured liquid was inoculated onto Simmons' agar medium containing 250 mg/L of kanamycin (2 g/L of sodium citrate, 5 g/L of sodium chloride, 0.2 g/L of magnesium sulfate heptahydrate, 1 g/L of ammonium dihydrogenphosphate, 1 g/L of potassium dihydrogenphosphate, and 15 g/L of agar; pH: 6.8). A bacterial strain which was growing on the agar medium was selected to gain a strain in which the above-mentioned plasmid was incorporated to the chromosome of the KNK005ΔphaZ1,2,6 strain. This strain was subjected to two-generation culturing on a nutrient broth medium (manufactured by the company Difco), and then diluted and applied onto a nutrient agar medium containing 15% of sucrose. In this way, the bacterial strain which was growing was gained as a plasmid-dropped-out strain. Furthermore, one bacterial strain was isolated in which the 793$^{th}$ base G of the nagE structural gene on the chromosome was substituted with C according to an analysis based on a DNA sequencer. This mutation-introduced strain was named a KNK005ΔphaZ1,2,6/nagEG793C strain. The resultant KNK005ΔphaZ1,2,6/nagEG793C strain was a strain in which: a sequence from the initiation codon to the termination codon of each of phaZ6 and phaZ1 genes on the chromosome of the *C. necator* H16 strain was deleted; a sequence from the 16$^{th}$ codon of the phaZ2 gene thereon to the termination codon thereof was deleted; a gene encoding a PHA synthetase having an amino acid sequence described in SEQ ID NO: 2 was introduced onto the chromosome; and G which was the 793$^{th}$ base of the nagE structural gene was substituted with C.

Furthermore, a plasmid for gene-disruption was produced. The production was performed as follows:

By PCR using a synthesized oligo DNA, a DNA fragment (SEQ ID NO: 12) was yielded which had base sequences at the upstream side and the downstream side of the nagR structural gene. The resultant DNA fragment was digested with a restriction enzyme SwaI. This DNA was linked to a vector pNS2X-sacB digested with SwaI in the same way and described in JP 2007-259708 A through a DNA ligase (Ligation High (manufactured by Toyobo Co., Ltd.)) to produce a plasmid vector pNS2X-sacB+nagRUD for gene-disruption, having base sequences on the upstream side and the downstream side of the nagR structural gene.

Next, the plasmid vector pNS2X-sacB+nagRUD for gene-disruption was used to produce a gene disrupted strain, i.e., KNK005ΔphaZ1,2,6/nagEG793C,dR strain in the same way as described above, using the KNK005ΔphaZ1,2,6/nagEG793C strain as a parent strain.

The KNK005ΔphaZ1,2,6/naEG793C,dR strain was a strain in which: the sequence from the initiation codon to the termination codon of each of the phaZ6 and phaZ1 genes on the chromosome of the *C. necator* H16 strain was deleted; the sequence from the 16$^{th}$ codon of the phaZ2 gene to the termination codon thereof was deleted; the gene encoding the PHA synthetase having the amino acid sequence described in SEQ ID NO: 2 was introduced onto the chromosome; G which was the 793$^{th}$ base of the nagE structural gene was substituted with C; and further a sequence from the initiation codon to the terminal codon of the nagR gene was deleted.

Furthermore, a plasmid for chromosome-introduction was produced. The production was performed as follows: By PCR using a synthesized oligo DNA, a DNA fragment (SEQ ID NO: 13) was yielded which had base sequences at the upstream side and the downstream side of a phaZ2 gene of a *C. necator* H16 strain. This DNA fragment was digested with a restriction enzyme SwaI, and then linked to a vector pNS2X-sacB digested with SwaI in the same way and described in JP 2007-259708 A through a DNA ligase (Ligation High (manufactured by Toyobo Co., Ltd.)) to yield pNS2X-sacB+Z2UDMS. Next, by PCR using an artificial gene synthesis and a synthesized oligo DNA, a DNA fragment (SEQ ID NO: 14) was yielded which had a Poe1 promoter, a CCR gene, and an EMD gene. This DNA fragment was digested with restriction enzymes EcoRI and SpeI, and the resultant DNA fragment was linked to the pNS2X-sacB+Z2UDMS digested with MunI and SpeI through a DNA ligase (Ligation High (manufactured by Toyobo Co., Ltd.)) to yield a plasmid vector pNS2X-sacB+Z2::Poe1-ccr-emd for chromosome-introduction.

Furthermore, the plasmid vector pNS2X-sacB+Z2::Poe1-ccr-emd for chromosome-introduction was used to produce a gene disrupted strain KNK005ΔphaZ1,2,6/nagEG793C, dR/Z2::Poe1-ccr-emd, using the KNK005ΔphaZ1,2,6/nagEG793C,dR strain as a parent strain in the same way as described above.

The KNK005ΔphaZ1,2,6/nagEG793C,dR/Z2::Poe1-ccr-emd strain was a strain in which: the sequence from the initiation codon to the termination codon of each of the phaZ6 and phaZ1 genes on the chromosome of the *C. necator* H16 strain was deleted; the sequence from the 16$^{th}$ codon of the phaZ2 gene to the termination codon thereof was deleted; the gene encoding the PHA synthetase having the amino acid sequence described in SEQ ID NO: 2 was introduced onto the chromosome; G which was the 793$^{th}$ base of the nagE structural gene was substituted with C; the sequence from the initiation codon to the termination codon of the nagR gene was deleted; and further one copy of the CCR gene and one copy of the EMD gene were introduced onto the chromosome.

By PCR using a synthesized oligo DNA, a DNA fragment (SEQ ID NO: 15) was yielded which had base sequences at the upstream side and the downstream side of a phaZ6 gene of a *C. necator* H16 strain. This DNA fragment was digested with a restriction enzyme SwaI, and linked to a vector pNS2X-sacB digested with SwaI and described in JP 2007-259708 A through a DNA ligase (Ligation High (manufactured by Toyobo Co., Ltd.)) to produce a vector pNS2X-sacB+Z6UDMS. Next, the DNA fragment (SEQ ID NO: 14), which had the Poe1 promoter, the CCR gene, and the EMD gene, was digested with restriction enzymes EcoRI and SpeI, and the resultant DNA fragment was linked to the vector pNS2X-sacB+Z6UDMS digested with MunI and SpeI through a DNA ligase (Ligation High (manufactured by Toyobo Co., Ltd.)) to yield a plasmid vector pNS2X-sacB+Z6::Poe1-ccr-emd for chromosome-introduction.

Furthermore, the plasmid vector pNS2X-sacB+Z6::Poe1-ccr-emd for chromosome-introduction was used to produce a gene-introduced strain KNK005ΔphaZ1,2,6/nagEG793C, dR/Z2,Z6::Poe1-ccr-emd, using the KNK005ΔphaZ1,2,6/nagEG793C,dR/Z2::Poe1-ccr-emd as a parent strain in the same way as described above.

The KNK005ΔphaZ1,2,6/nagEG793C,dR/Z2,Z6::Poe1-ccr-emd strain was a strain in which: the sequence from the initiation codon to the termination codon of each of the phaZ6 and phaZ1 genes on the chromosome of the *C. necator* H16 strain was deleted; the sequence from the 16$^{th}$ codon of the phaZ2 gene to the termination codon thereof was deleted; the gene encoding the PHA synthetase having the amino acid sequence described in SEQ ID NO: 2 was introduced onto the chromosome; G which was the 793rd base of the nagE structural gene was substituted with C; the sequence from the initiation codon to the termination codon of the nagR gene was deleted; and further two copies of the CCR gene and two copies of the EMD gene were introduced onto the chromosome.

(Example 2) Production of pCUP2-trc-MFE2yl/ KNK005ΔphaZ1,2,6/naEG793C,dR/Z2,Z6::Poe1-ccr-emd Strain The same electrical introduction as described in Example 1 was used to introduce the plasmid vector pCUP2-trc-MFE2yl produced in Production Example 1 into the KNK0054phaZ1,2,6/nagEG793C,dR/Z2,Z6::Poe1-ccr-emd strain described in Production Example 2 to gain a pCUP2-trc-MFE2yl/KNK005ΔphaZ1,2,6/nagEG793C,dR/Z2,Z6::Poe1-ccr-emd strain.

(Production Example 3) Production of KNK143 S/Z6::Poe1-ccr-emd Strain

Initially, a plasmid vector bAO/pBlu/SacB-Km for chromosome-substitution, which is described in JP 2013-9627 A, was used to produce a promoter- and SD-sequence-inserted strain, i.e., an ACP-bktB/ΔphaZ1,2,6/nagEG793C,dR strain, using the KNK005ΔphaZ1,2,6/nagEG793C,dR strain as a parent strain in the same way as in production Example 2.

The ACP-bktB/ΔphaZ1,2,6/nagEG793C,dR strain was a strain in which: the sequence from the initiation codon to the termination codon of each of phaZ6 and phaZ1 genes on the chromosome of the C. necator H16 strain was deleted; the sequence from the 16th codon of the phaZ2 gene to the termination codon thereof was deleted; the gene encoding the PHA synthetase having an amino acid sequence described in SEQ ID NO: 2 was introduced onto the chromosome; G which was the 793rd base of the nagE structural gene was substituted with C; the sequence from the initiation codon to the termination codon of the nagR gene was deleted; and further a DNA made of a base sequence containing a promoter and a ribosome-binding-sequence of the phaC gene of A. caviae was inserted to the position immediately before the initiation codon of a bktB (β ketothiolase) gene.

Next, a plasmid vector pNS2X-sacB+phaJ4bU-trc-phaJ4b for promoter- and SD-sequence-insertions, which is described in WO 2015/115619, was used to produce a promoter- and SD-sequence-inserted strain, i.e., an ACP-bktB/ΔphaZ1,2,6/nagEG793C,dR/trc-J4b strain, using the ACP-bktB/ΔphaZ1,2,6/nagEG793C,dR strain as a parent strain in the same way as in Production Example 2.

The ACP-bktB/ΔphaZ1,2,6/nagEG793C,dR/trc-J4b strain was a strain in which: the sequence from the initiation codon to the termination codon of each of the phaZ6 and phaZ1 genes on the chromosome of the C. necator H16 strain was deleted; the sequence from the 16th codon of the phaZ2 gene to the termination codon thereof was deleted; the gene encoding the PHA synthetase having the amino acid sequence described in SEQ ID NO: 2 was introduced onto the chromosome; G which was the 793rd base of the nagE structural gene was substituted with C; the sequence from the initiation codon to the terminal codon of the nagR gene was deleted; the DNA made of the base sequence containing the promoter and the ribosome-binding-sequence of the phaC gene of A. caviae was inserted to the position immediately before the initiation codon of the bktB gene; and further a DNA made of a base sequence containing the trc promoter and a ribosome-binding-sequence was inserted to the position immediately before the initiation codon of the phaJ4b gene.

Furthermore, a vector pBlueASRU for chromosome-substitution, which is described in JP 2008-29218 A, was used to produce a KNK144S by the method described in Production Example 2, using the ACP-bktB/ΔphaZ1,2,6/nagEG793C,dR/trc-J4b as a parent strain.

The KNK144S strain was a strain in which: the sequence from the initiation codon to the termination codon of each of the phaZ6 and phaZ1 genes on the chromosome of the C. necator H16 strain was deleted; the sequence from the 16th codon of the phaZ2 gene to the termination codon thereof was deleted; the gene encoding the PHA synthetase having the amino acid sequence described in SEQ ID NO: 2 was introduced onto the chromosome; G which was the 793rd base of the nagE structural gene was substituted with C; the sequence from the initiation codon to the terminal codon of the nagR gene was deleted; the DNA made of the base sequence containing the promoter and the ribosome-binding-sequence of the phaC gene of A. caviae was inserted to the position immediately before the initiation codon of the bktB gene; the DNA made of the base sequence containing the trc promoter and the ribosome-binding-sequence was inserted to the position immediately before the initiation codon of the phaJ4b gene; and further a terminal codon and a restriction enzyme NheI cut-moiety were produced in the phaA structural gene sequence.

Next, a plasmid was produced for promoter, ribosome-binding-sequence, and gene insertions. The production was performed as follows:

Next, PCR making use of an artificial gene synthesis and a synthesized oligo DNA was used to yield a DNA fragment into which a base sequence described in SEQ ID NO: 16 was introduced, this fragment including a ribosome-binding-sequence, a CCR gene, and an EMD gene. This DNA fragment was digested with restriction enzymes MunI and SpeI. The resultant DNA fragment was linked to a product in which the plasmid vector pNS2X-sacB+Z2UDMS was cut with MunI and SpeI, so as to yield a plasmid vector pNS2X-sacB+Z2U-ccr-emd-Z2D.

Next, by PCR using a synthesized oligo DNA, a DNA fragment (SEQ ID NO: 17) was yielded which had a trc promoter. This DNA fragment was digested with MunI, and the resultant was linked to a product in which the above-mentioned plasmid vector pNS2X-sacB+Z2U-ccr-emd-Z2D was cut with MunI. From the resultant plasmids, a PCR was used to select a plasmid to which the trc promoter sequence was linked in a direction along which ccr and emd were positioned at the downstream side of the trc promoter sequence. In this way, a plasmid vector pNS2X-sacB+Z2U-trc-ccr-emd-Z2D for promoter, ribosome-binding-sequence and gene insertions was yielded.

Next, the plasmid vector pNS2X-sacB+Z2U-trc-ccr-emd-Z2D for promoter, ribosome-binding-sequence, and gene insertions was used to produce a KNK143S strain by the method described in Production Example 2, using the KNK144S as a parent strain.

The KNK143S strain was a strain in which: the sequence from the initiation codon to the termination codon of each of phaZ6 and phaZ1 genes on the chromosome of the C. necator H16 strain was deleted; the sequence from the 16th codon of the phaZ2 gene to the termination codon thereof was deleted; the gene encoding the PHA synthetase having the amino acid sequence described in SEQ ID NO: 2 was introduced onto the chromosome; G which was the 793rd base of the nagE structural gene was substituted with C; the sequence from the initiation codon to the terminal codon of the nagR gene was deleted; the DNA made of the base sequence containing the promoter and the ribosome-binding-sequence of the phaC gene of *A. caviae* was inserted to the position immediately before the initiation codon of the bktB gene; the DNA made of the base sequence containing the trc promoter and the ribosome-binding-sequence was inserted to the position immediately before the initiation codon of the phaJ4b gene; the termination codon and the restriction enzyme NheI cut-moiety were produced in the phaA structural gene sequence; and further the trc promoter, the ribosome-binding-sequence, and the CCR and EMD genes were inserted to the position where the phaZ2 gene was originally presented.

Furthermore, the plasmid vector pNS2X-sacB+Z6::Poe1-ccr-emd for chromosome-introduction, which is described in Production Example 2, was used to produce a KNK143S/Z6::Poe1-ccr-emd strain for gene-introduction by the method described in Production Example 2, using the KNK143S as a parent strain.

The KNK143S/Z6::Poe1-ccr-emd strain was a strain in which: the sequence from the initiation codon to the termination codon of each of phaZ6 and phaZ1 genes on the chromosome of the *C. necator* H16 strain was deleted; the sequence from the 16$^{th}$ codon of the phaZ2 gene to the termination codon thereof was deleted; the gene encoding the PHA synthetase having the amino acid sequence described in SEQ ID NO: 2 was introduced onto the chromosome; G which was the 793$^{rd}$ base of the nagE structural gene was substituted with C; the sequence from the initiation codon to the terminal codon of the nagR gene was deleted; the DNA made of the base sequence containing the promoter and the ribosome-binding-sequence of the phaC gene of *A. caviae* was inserted to the position immediately before the initiation codon of the bktB gene; the DNA made of the base sequence containing the trc promoter and the ribosome-binding-sequence was inserted to the position immediately before the initiation codon of the phaJ4b gene; the termination codon and the restriction enzyme NheI cut-moiety were produced in the phaA structural gene sequence; and further two copies of the CCR gene and two copies of the EMD gene were inserted onto the chromosome.

(Example 3) Production of pCUP2-trc-MFE2yl/KNK143S/Z6::Poe1-ccr-emd Strain

The same electrical introduction as described in Example 1 was used to introduce the plasmid vector pCUP2-trc-MFE2yl produced in Production Example 1 into the KNK143S/Z6::Poe1-ccr-emd strain described in Production Example 3 to gain a pCUP2-trc-MFE2yl/KNK143S/Z6::Poe1-ccr-emd strain.

(Comparative Example 1) PHA Production Using KNK005 Strain

The composition of a seed medium was set as follows: 1 w/v % of a meat-extract, 1 w/v % of bacto-trypton, 0.2 w/v % of a yeast-extract, 0.9 w/v % of $Na_2HPO_4 \cdot 12H_2O$, and 0.15 w/v % $KH_2PO_4$.

A producing medium used for the PHA production was set as follows: 1.1 w/v % of $Na_2HPO_4 \cdot 12H_2O$, 0.19 w/v % of $KH_2PO_4$, 0.13 w/v % of $(NH_4)_2SO_4$, 0.1 w/v % of $MgSO_4 \cdot 7H_2O$, 0.1 v/v % of trace metal salt solution (solution in which into a 0.1 N solution of hydrochloric acid were dissolved 1.6 w/v % of $FeCl_3 \cdot 6H_2O$, 1 w/v % of $CaCl_2 \cdot 2H_2O$, 0.02 w/v % of $CoCl_2 \cdot 6H_2O$, 0.016 w/v % of $CuSO_4 \cdot 5H_2O$, and 0.012 w/v % of $NiCl_2 \cdot 6H_2O$. For a carbon source, a palm kernel oil was added to the medium to give a concentration of 1.5 w/v %.

A glycerol stock (50 μL) of a KNK005 strain was inoculated into the seed medium (5 mL), and this system was shaken at a culturing temperature of 30° C. for 24 hours to culture the strain. The resultant culture solution was used as a seed.

In the PHA production culturing, the seed was inoculated, in an amount of 1.0 v/v %, into a Sakaguchi flask in which 50 mL of the producing medium was put, and the seed was shaken and cultured at a culturing temperature of 30° C. The bacterial cells were cultured for 72 hours. Thereafter, the cells were collected by centrifugal separation, washed with methanol, and freeze-dried. The weight of the dried bacterial cells was then measured.

The PHA production amount was calculated out as follows: To the resultant dry bacterial cells was added chloroform in an amount of 100 mL per gram of the cells. At room temperature, the resultant was stirred a whole day and night. Any PHA in the bacterial cells was extracted. The bacterial cell residue was filtrated away, and an evaporator was used to concentrate the residue until the total volume thereof turned into 1/3. Thereafter, thereto was gradually added hexane in a volume three times the concentrated liquid volume. The liquid was allowed to stand still for 1 hour while slowly stirred. The precipitated PHA was filtrated away, and the PHA was vacuum-dried at 50° C. for 3 hours. The weight of the dried PHA was measured to calculate out the PHA production amount. The results are shown in Table 1.

The 3HH composition proportion in the produced PHA was measured by gas chromatography as follows: To about 20 mg of the dried PHA were added 2 mL of a sulfuric-acid/methanol mixed solution (15/85) and 2 mL of chloroform, and the system was airtightly sealed. The system was heated at 100° C. for 140 minutes to yield a methyl ester of a PHA decomposed product. After the system was cooled, to this product was added 1.5 g of sodium hydrogencarbonate bit by bit to neutralize the product. The system was allowed to stand still until the generation of carbon dioxide gas was stopped. Thereto was added 4 mL of diisopropyl ether, and the entire components were sufficiently mixed with each other. Thereafter, the resultant was subjected to centrifugal separation. A capillary gas chromatography was used to analyze the monomer unit composition of the PHA decomposed product in the supernatant. The used gas chromatograph was an instrument GC-17A manufactured by Shimadzu Corporation, and the used capillary column was a column NEUTRA BOND-1 (column length: 25 m, column inside diameter: 0.25 mm, and a liquid membrane thickness: 0.4 μm) manufactured by GL Sciences Inc. The used carrier gas was He, and the column inlet pressure was set to 100 kPa. Any sample was injected in a volume of 1 μL. The temperature conditions were as follows: the temperature was raised at a rate of 8° C./minute from a starting temperature of 100° C. to 200° C., and the temperature was raised at a rate of 30° C./minute from 200° C. to 290° C. Under the above-mentioned conditions, the analysis was made. The resultant composition proportion of 3HH in the PHA is shown in Table 1.

The PHA produced in the present comparative example was a P(3HB-co-3HH) containing 2.9% by mol of 3HH units.

(Example 4) PHA Production Using
pCUP2-trc-MFE2yl/KNK005 Strain

The composition of a seed medium was rendered the same as described in Comparative Example 1. When a plasmid vector introduced strain of this example was cultured in the seed medium, kanamycin was added to the seed medium to give a final concentration of 100 μg/mL.

The composition of a producing medium used for the PHA production, and a carbon source used therein were rendered the same as described in Comparative Example 1.

The pCUP2-trc-MFE2yl/KNK005 strain produced in Example 1 was cultured in the same way as in Comparative Example 1, and then the PHA production amount, and the composition proportion of 3HH were calculated in the same way as in Comparative Example 1. The resultant PHA production amount and 3HH composition proportion are shown in Table 1.

The PHA produced in the present example was a P(3HB-co-3HH) having a 3HH composition proportion of 6.3% by mol. In other words, the introduction of the MFE2 gene attained the production of a copolymerized PHA including a larger amount of 3HH units than the copolymerized PHA produced in Comparative Example 1.

(Comparative Example 2) PHA Production Using
KNK005ΔphaZ1,2,6/nagEG793C,dR/Z2,Z6::Poe1-ccr-emd Strain The composition of a seed medium was rendered the same as described in Comparative Example 1. The composition of a producing medium used for the PHA production was rendered the same as described in Comparative Example 1, and for a carbon source, no palm kernel oil was used, but a 40 w/v % glucose solution in water was used as a single carbon source. This solution was added into the producing medium to give a concentration of 2.0 w/v %.

The KNK005ΔphaZ1,2,6/nagEG793C,dR/Z2,Z6::Poe1-ccr-emd strain produced in Production Example 2 was cultured in the same way as in Comparative Example 1, and the resultant PHA production amount and the 3HH composition proportion were calculated in the same way as in Comparative Example 1. The resultant PHA production amount and 3HH composition proportion are shown in Table 1.

The PHA produced in the present comparative example was a PHB, which contained no 3HH units.

(Example 5) PHA Production Using pCUP2-trc-MFE2yl/KNK005ΔphaZ1,2,6/nagEG793C,dR/Z2,Z6::Poe1-ccr-emd Strain The composition of a seed medium was rendered the same as described in Comparative Example 1. When a plasmid vector introduced strain of this example was cultured in the seed medium, kanamycin was added to the seed medium to give a final concentration of 100 μg/mL.

The composition of a producing medium used for the PHA production was rendered the same as described in Comparative Example 1, and for a carbon source, no palm kernel oil was used, but a 40 w/v % glucose solution in water was used as a single carbon source. This solution was added into the producing medium to give a concentration of 2.0 w/v %.

The pCUP2-trc-MFE2yl/KNK005ΔphaZ1,2,6/nagEG793C,dR/Z2,Z6::Poe1-ccr-emd strain produced in Example 2 was cultured in the same way as in Comparative Example 1, and the resultant PHA production amount and 3HH composition proportion were calculated in the same way as in Comparative Example 1. The resultant PHA production amount and 3HH composition proportion are shown in Table 1.

The PHA produced in the present example was a P(3HB-co-3HH) containing 3HH units in a proportion of 1.4% by mol. In Comparative Example 2, the homo-polymerized PHA, which contained no 3HH units, was produced while in the present example, the introduction of the MFE2 gene attained the production of the copolymerized PHA containing 3HH unit.

(Comparative Example 3) PHA Production Using
KNK143S/Z6::Poe1-ccr-emd Strain

The composition of a seed medium was rendered the same as described in Comparative Example 1. The composition of a producing medium used for the PHA production was rendered the same as described in Comparative Example 1, and for a carbon source, no palm kernel oil was used, but a 40 w/v % glucose solution in water was used as a single carbon source. This solution was added into the producing medium to give a concentration of 2.0 w/v %.

The KNK143S/Z6::Poe1-ccr-emd strain produced in Production Example 3 was cultured in the same way as in Comparative Example 1, and the resultant PHA production amount and 3HH composition proportion were calculated in the same way as in Comparative Example 1. The resultant PHA production amount and 3HH composition proportion are shown in Table 1.

The PHA produced in the present comparative example was a P(3HB-co-3HH) containing 3HH units in a proportion of 1.1% by mol.

(Example 6) PHA Production Using
pCUP2-trc-MFE2yl/KNK143S/Z6::Poe1-ccr-emd Strain The composition of a seed medium was rendered the same as described in Comparative Example 1. The composition of a producing medium used for the PHA production was rendered the same as described in Comparative Example 1, and for a carbon source, no palm kernel oil was used, but a 40 w/v % glucose solution in water was used as a single carbon source. This solution was added into the producing medium to give a concentration of 2.0 w/v %.

The pCUP2-trc-MFE2yl/KNK143S/Z6::Poe1-ccr-emd strain produced in Example 3 was cultured in the same way as in Comparative Example 1, and the resultant PHA production amount and 3HH composition proportion were calculated in the same way as in Comparative Example 1. The resultant PHA production amount and 3HH composition proportion are shown in Table 1.

The PHA produced in the present example was a P(3HB-co-3HH) containing 3HH units in a proportion of 4.7% by mol. In other words, the introduction of the MFE2 gene attained the production of a copolymerized PHA containing a larger amount of 3HH units than the copolymerized PHA produced in Comparative Example 3.

TABLE 1

| Bacterial strain name | | Introduced gene | Carbon source | PHA production amount (g/L) | 3HH composition proportion (% by mol) |
|---|---|---|---|---|---|
| Comparative Example 1 | KNK005 | — | Palm kernel oil | 14.7 | 2.9 |
| Example 4 | pCUP2 - trc - MFE2y1/KNK005 | MFE2 | Palm kernel oil | 14.1 | 6.3 |
| Comparative Example 2 | KNK005 ΔphaZ1, 2, 6/nagEG793C, dR/Z2, Z6 :: Poe1 - ccr - emd | ccr + emd | Glucose | 7.4 | 0 |
| Example 5 | pCUP2 - trc - MFE2y1/KNK005 ΔphaZ1, 2, 6/nagEG793C, dR/Z2, Z6 :: Poe1 - ccr - emd | ccr + emd + MFE2 | Glucose | 7.2 | 1.4 |
| Comparative Example 3 | KNK143S/Z6 :: Poe1 - ccr - emd | ccr + emd | Glucose | 7.2 | 1.1 |
| Example 6 | pCUP2 - trc - MFE2y1/KNK143S/Z6 :: Poe1 - ccr - emd | ccr + emd + MFE2 | Glucose | 6.6 | 4.7 |

The invention claimed is:

1. A transformant that produces a copolymerized polyhydroxyalkanoate (PHA) comprising a 3-hydroxyhexanoic acid (3HH) unit, wherein the transformant is a prokaryotic microorganism into which a gene encoding an enzyme having trans-2-enoyl-CoA hydratase activity and (R)-3-hydroxyacyl-CoA dehydrogenase activity is introduced, wherein the prokaryotic microorganism comprises a PHA synthetase gene capable of synthesizing the copolymerized PHA comprising the 3HH units, and the gene encoding an enzyme having trans-2-enoyl-CoA hydratase activity and (R)-3-hydroxyacyl-CoA dehydrogenase activity is derived from an eukaryote,
   wherein the prokaryotic microorganism is *Cupriavidus necator*, and
   wherein the gene encoding the enzyme having trans-2-enoyl-CoA hydratase activity and (R)-3-hydroxyacyl-CoA dehydrogenase activity is a gene derived from *Yarrowia lipolytica.*

2. The transformant according to claim 1, into which a gene encoding a crotonyl-CoA reductase (CCR) is further introduced.

3. The transformant according to claim 2, into which a gene encoding an ethylmalonyl-CoA decarboxylase is further introduced.

4. A transformant that produces a copolymerized polyhydroxyalkanoate (PHA) comprising a 3-hydroxyhexanoic acid (3HH) unit, wherein the transformant is a prokaryotic microorganism into which a gene encoding an enzyme having trans-2-enoyl-CoA hydratase activity and (R)-3-hydroxyacyl-CoA dehydrogenase activity is introduced, wherein the prokaryotic microorganism comprises a PHA synthetase gene capable of synthesizing the copolymerized PHA comprising the 3HH units, and the gene encoding an enzyme having trans-2-enoyl-CoA hydratase activity and (R)-3-hydroxyacyl-CoA dehydrogenase activity is derived from an eukaryote,
   wherein the prokaryotic microorganism is *Cupriavidus necator*, and
   wherein the gene encoding the enzyme having trans-2-enoyl-CoA hydratase activity and (R)-3-hydroxyacyl-CoA dehydrogenase activity is a gene derived from *Drosophila melanogaster.*

5. A method for producing a copolymerized PHA containing a 3HH unit, comprising:
   culturing the transformant of claim 1.

6. The method according to claim 5, wherein the copolymerized PHA is a copolymer of 3-hydroxybutyric acid (3HB) and 3-hydroxyhexanoic acid (3HH), P(3HB-co-3HH).

7. The method according to claim 5, wherein the transformant is cultured in a medium comprising an oil and fat or an aliphatic acid as a carbon source.

8. The method according to claim 5, wherein the transformant is cultured in a medium comprising a saccharide as a carbon source.

9. The method according to claim 6, wherein the transformant is cultured in a medium comprising an oil and fat or an aliphatic acid as a carbon source.

10. The method according to claim 6, wherein the transformant is cultured in a medium comprising a saccharide as a carbon source.

11. The transformant according to claim 4, into which a gene encoding a crotonyl-CoA reductase (CCR) is further introduced.

12. The transformant according to claim 4, into which a gene encoding an ethylmalonyl-CoA decarboxylase is further introduced.

13. A method for producing a copolymerized PHA comprising a 3HH unit, comprising:
   culturing the transformant of claim 4.

14. The method according to claim 13, wherein the copolymerized PHA is a copolymer of 3-hydroxybutyric acid (3HB) and 3-hydroxyhexanoic acid (3HH), P(3HB-co-3HH).

15. The method according to claim 13, wherein the transformant is cultured in a medium comprising an oil and fat or an aliphatic acid as a carbon source.

16. The method according to claim 13, wherein the transformant is cultured in a medium comprising a saccharide as a carbon source.

17. The method according to claim 14, wherein the transformant is cultured in a medium comprising an oil and fat or an aliphatic acid as a carbon source.

18. The method according to claim 14, wherein the transformant is cultured in a medium comprising a saccharide as a carbon source.

* * * * *

SEQUENCE LISTING

<160> NUMBER OF SEQ ID NOS: 17

<210> SEQ ID NO 1
<211> LENGTH: 594
<212> TYPE: PRT
<213> ORGANISM: Aeromonas caviae

<400> SEQUENCE: 1

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg

-continued

```
                245                 250                 255
Pro Gln Asn Ser Leu Val Ala Trp Leu Val Ala Gln Gly Gln Thr Val
            260                 265                 270
Phe Met Ile Ser Trp Arg Asn Pro Gly Val Ala Gln Ala Gln Ile Asp
        275                 280                 285
Leu Asp Asp Tyr Val Val Asp Gly Val Ile Ala Ala Leu Asp Gly Val
    290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg Arg
                325                 330                 335
Gln Lys Gln Arg Val Arg Thr Ala Thr Leu Phe Thr Thr Leu Leu Asp
            340                 345                 350
Phe Ser Gln Pro Gly Glu Leu Gly Ile Phe Ile His Glu Pro Ile Ile
        355                 360                 365
Ala Ala Leu Glu Ala Gln Asn Glu Ala Lys Gly Ile Met Asp Gly Arg
    370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
            420                 425                 430
His Asn Ser Leu Leu Arg Arg Leu Tyr Leu Glu Asn Gln Leu Val Lys
        435                 440                 445
Gly Glu Leu Lys Ile Arg Asn Thr Arg Ile Asp Leu Gly Lys Val Lys
    450                 455                 460
Thr Pro Val Leu Leu Val Ser Ala Val Asp Asp His Ile Ala Leu Trp
465                 470                 475                 480
Gln Gly Thr Trp Gln Gly Met Lys Leu Phe Gly Gly Glu Gln Arg Phe
                485                 490                 495
Leu Leu Ala Glu Ser Gly His Ile Ala Gly Ile Ile Asn Pro Pro Ala
            500                 505                 510
Ala Asn Lys Tyr Gly Phe Trp His Asn Gly Ala Glu Ala Glu Ser Pro
        515                 520                 525
Glu Ser Trp Leu Ala Gly Ala Thr His Gln Gly Gly Ser Trp Trp Pro
    530                 535                 540
Glu Met Met Gly Phe Ile Gln Asn Arg Asp Glu Gly Ser Glu Pro Val
545                 550                 555                 560
Pro Ala Arg Val Pro Glu Glu Gly Leu Ala Pro Ala Pro Gly His Tyr
                565                 570                 575
Val Lys Val Arg Leu Asn Pro Val Phe Ala Cys Pro Thr Glu Glu Asp
            580                 585                 590
Ala Ala
```

<210> SEQ ID NO 2
<211> LENGTH: 594
<212> TYPE: PRT
<213> ORGANISM: Aeromonas caviae

<400> SEQUENCE: 2

```
Met Ser Gln Pro Ser Tyr Gly Pro Leu Phe Glu Ala Leu Ala His Tyr
1               5                   10                  15
Asn Asp Lys Leu Leu Ala Met Ala Lys Ala Gln Thr Glu Arg Thr Ala
```

-continued

```
                20                  25                  30
Gln Ala Leu Leu Gln Thr Asn Leu Asp Asp Leu Gly Gln Val Leu Glu
             35                  40                  45
Gln Gly Ser Gln Gln Pro Trp Gln Leu Ile Gln Ala Gln Met Asn Trp
         50                  55                  60
Trp Gln Asp Gln Leu Lys Leu Met Gln His Thr Leu Leu Lys Ser Ala
 65                  70                  75                  80
Gly Gln Pro Ser Glu Pro Val Ile Thr Pro Glu Arg Ser Asp Arg Arg
                 85                  90                  95
Phe Lys Ala Glu Ala Trp Ser Glu Gln Pro Ile Tyr Asp Tyr Leu Lys
                100                 105                 110
Gln Ser Tyr Leu Leu Thr Ala Arg His Leu Leu Ala Ser Val Asp Ala
            115                 120                 125
Leu Glu Gly Val Pro Gln Lys Ser Arg Glu Arg Leu Arg Phe Phe Thr
        130                 135                 140
Arg Gln Tyr Val Ser Ala Met Ala Pro Ser Asn Phe Leu Ala Thr Asn
145                 150                 155                 160
Pro Glu Leu Leu Lys Leu Thr Leu Glu Ser Gly Gly Gln Asn Leu Val
                165                 170                 175
Arg Gly Leu Ala Leu Ala Glu Asp Leu Glu Arg Ser Ala Asp Gln
            180                 185                 190
Leu Asn Ile Arg Leu Thr Asp Glu Ser Ala Phe Glu Leu Gly Arg Asp
            195                 200                 205
Leu Ala Leu Thr Pro Gly Arg Val Val Gln Arg Thr Glu Leu Tyr Glu
        210                 215                 220
Leu Ile Gln Tyr Ser Pro Thr Thr Glu Thr Val Gly Lys Thr Pro Val
225                 230                 235                 240
Leu Ile Val Pro Pro Phe Ile Asn Lys Tyr Tyr Ile Met Asp Met Arg
                245                 250                 255
Pro Gln Asn Ser Leu Val Ala Trp Leu Val Ala Gln Gly Gln Thr Val
            260                 265                 270
Phe Met Ile Ser Trp Arg Asn Pro Gly Val Ala Gln Ala Gln Ile Asp
        275                 280                 285
Leu Asp Asp Tyr Val Val Asp Gly Val Ile Ala Ala Leu Asp Gly Val
        290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg Arg
                325                 330                 335
Gln Lys Gln Arg Val Arg Thr Ala Thr Leu Phe Thr Thr Leu Leu Asp
            340                 345                 350
Phe Ser Gln Pro Gly Glu Leu Gly Ile Phe Ile His Glu Pro Ile Ile
        355                 360                 365
Ala Ala Leu Glu Ala Gln Asn Glu Ala Lys Gly Ile Met Asp Gly Arg
        370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
            420                 425                 430
His Asn Ser Leu Leu Arg Arg Leu Tyr Leu Glu Asn Gln Leu Val Lys
        435                 440                 445
```

-continued

Gly Glu Leu Lys Ile Arg Asn Thr Arg Ile Asp Leu Gly Lys Val Lys
            450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 3
<211> LENGTH: 901
<212> TYPE: PRT
<213> ORGANISM: Yarrowia lipolytica

<400> SEQUENCE: 3

Met Ser Gly Glu Leu Arg Tyr Asp Gly Lys Val Val Ile Val Thr Gly
1               5                   10                  15

Ala Gly Gly Gly Leu Gly Lys Ala Tyr Ala Leu Phe Tyr Gly Ser Arg
                20                  25                  30

Gly Ala Ser Val Val Val Asn Asp Leu Gly Gly Asp Phe Lys Gly Asp
            35                  40                  45

Gly Ala Gln Ala Gly Ser Gly Lys Arg Val Ala Asp Val Val Asp
        50                  55                  60

Glu Ile Val Ser Lys Gly Gly Lys Ala Val Ala Asn Tyr Asp Ser Val
65                  70                  75                  80

Glu Asn Gly Asp Lys Ile Val Glu Thr Ala Val Lys Ala Phe Gly Ser
                85                  90                  95

Val His Ile Val Ile Asn Asn Ala Gly Ile Leu Arg Asp Ile Ser Phe
            100                 105                 110

Lys Lys Met Thr Asp Lys Asp Trp Asp Leu Val Tyr Lys Val His Val
        115                 120                 125

Phe Gly Ala Tyr Lys Val Thr Arg Ala Ala Trp Pro Tyr Phe Arg Lys
    130                 135                 140

Gln Lys Tyr Gly Arg Val Ile Ser Thr Ser Ser Ala Ala Gly Leu Tyr
145                 150                 155                 160

Gly Asn Phe Gly Gln Thr Asn Tyr Ser Ala Ala Lys Leu Ala Leu Val
                165                 170                 175

Gly Phe Gly Glu Thr Leu Ala Lys Glu Gly Ala Lys Tyr Asn Ile Thr
            180                 185                 190

Ser Asn Val Ile Ala Pro Leu Ala Ala Ser Arg Met Thr Glu Thr Val
        195                 200                 205

Met Pro Glu Asp Ile Leu Lys Leu Leu Lys Pro Glu Tyr Val Val Pro
    210                 215                 220

```
Leu Val Gly Tyr Leu Thr His Asp Ser Val Thr Glu Ser Tyr Gly Ile
225                 230                 235                 240

Tyr Glu Val Gly Ala Gly Tyr Met Ala Lys Ile Arg Trp Glu Arg Gly
            245                 250                 255

Asn Gly Ala Val Phe Lys Gly Asp Asp Thr Phe Thr Pro Ser Ala Ile
            260                 265                 270

Leu Lys Arg Trp Asp Glu Val Thr Ser Phe Glu Ser Pro Thr Tyr Pro
            275                 280                 285

Asn Gly Pro Ala Asp Phe Phe Lys Tyr Ala Glu Glu Ser Val Lys Arg
            290                 295                 300

Pro Glu Asn Pro Gln Gly Pro Thr Val Ser Phe Lys Asp Gln Val Val
305                 310                 315                 320

Ile Val Thr Gly Ala Gly Ala Gly Ile Gly Arg Ala Tyr Ser His Leu
            325                 330                 335

Leu Ala Lys Leu Gly Ala Lys Val Val Asn Asp Phe Gly Asn Pro
            340                 345                 350

Gln Lys Val Val Asp Glu Ile Lys Ala Leu Gly Gly Ile Ala Val Ala
            355                 360                 365

Asp Lys Asn Asn Val Ile His Gly Glu Lys Val Val Gln Thr Ala Ile
370                 375                 380

Asp Ala Phe Gly Ala Val His Ala Val Val Asn Asn Ala Gly Ile Leu
385                 390                 395                 400

Arg Asp Lys Ser Phe Ala Asn Met Asp Asp Glu Met Trp Gln Leu Ile
            405                 410                 415

Phe Asp Val His Leu Asn Gly Thr Tyr Ser Val Thr Lys Ala Ala Trp
            420                 425                 430

Pro His Phe Leu Lys Gln Lys Tyr Gly Arg Val Ile Asn Thr Thr Ser
            435                 440                 445

Thr Ser Gly Ile Tyr Gly Asn Phe Gly Gln Ala Asn Tyr Ser Ala Ala
            450                 455                 460

Lys Ala Gly Ile Leu Gly Phe Ser Arg Ala Leu Ala Arg Glu Gly Glu
465                 470                 475                 480

Lys Tyr Asn Ile Leu Val Asn Thr Ile Ala Pro Asn Ala Gly Thr Ala
            485                 490                 495

Met Thr Ala Ser Val Phe Thr Glu Glu Met Leu Glu Leu Phe Lys Pro
            500                 505                 510

Asp Phe Ile Ala Pro Ile Thr Val Leu Leu Ala Ser Asp Gln Ala Pro
            515                 520                 525

Val Thr Gly Asp Leu Phe Glu Thr Gly Ser Ala Trp Ile Gly Gln Thr
            530                 535                 540

Arg Trp Gln Arg Ala Gly Gly Lys Ala Phe Asn Thr Lys Lys Gly Val
545                 550                 555                 560

Thr Pro Glu Met Val Arg Asp Ser Trp Ala Lys Ile Val Asp Phe Asp
            565                 570                 575

Asp Gly Asn Ser Thr His Pro Thr Thr Pro Ser Glu Ser Thr Thr Gln
            580                 585                 590

Ile Leu Glu Asn Ile Phe Asn Val Pro Asp Glu Glu Val Glu Glu Thr
            595                 600                 605

Ala Leu Val Ala Gly Pro Gly Gly Pro Gly Ile Leu Asn Lys Glu Gly
            610                 615                 620

Glu Pro Phe Asp Tyr Thr Tyr Thr Tyr Arg Asp Leu Ile Leu Tyr Asn
625                 630                 635                 640
```

-continued

```
Leu Gly Leu Gly Ala Lys Ala Asn Glu Leu Lys Tyr Val Phe Glu Gly
                645                 650                 655

Asp Asp Asp Phe Gln Thr Val Pro Thr Phe Gly Val Ile Pro Tyr Met
            660                 665                 670

Gly Gly Leu Ile Thr Thr Asn Tyr Gly Asp Phe Val Pro Asn Phe Asn
            675                 680                 685

Pro Met Met Leu Leu His Gly Glu Gln Tyr Leu Glu Ile Arg Gln Trp
    690                 695                 700

Pro Ile Pro Thr Asn Ala Thr Leu Glu Asn Lys Ala Lys Val Ile Asp
705                 710                 715                 720

Val Val Asp Lys Gly Lys Ala Ala Leu Leu Val Thr Ala Thr Thr Thr
                725                 730                 735

Thr Asn Lys Glu Thr Gly Glu Glu Val Phe Tyr Asn Glu Ser Ser Leu
            740                 745                 750

Phe Ile Arg Gly Ser Gly Gly Phe Gly Gly Lys Ser Thr Gly Thr Asp
            755                 760                 765

Arg Gly Ala Ala Thr Ala Ala Asn Lys Pro Pro Ala Arg Ala Pro Asp
    770                 775                 780

Phe Val Lys Glu Ile Lys Ile Gln Glu Asp Gln Ala Ala Ile Tyr Arg
785                 790                 795                 800

Leu Ser Gly Asp Tyr Asn Pro Leu His Ile Asp Pro Ala Phe Ala Ala
                805                 810                 815

Val Gly Asn Phe Asp Arg Pro Ile Leu His Gly Leu Cys Ser Phe Gly
            820                 825                 830

Val Ser Gly Lys Ala Leu Tyr Asp Gln Phe Gly Pro Phe Lys Asn Ala
            835                 840                 845

Lys Val Arg Phe Ala Gly His Val Phe Pro Gly Glu Thr Leu Lys Val
    850                 855                 860

Glu Gly Trp Lys Glu Gly Asn Lys Val Ile Phe Gln Thr Lys Val Val
865                 870                 875                 880

Glu Arg Gly Thr Thr Ala Ile Ser Asn Ala Ala Ile Glu Leu Phe Pro
                885                 890                 895

Lys Asp Ala Lys Leu
                900

<210> SEQ ID NO 4
<211> LENGTH: 598
<212> TYPE: PRT
<213> ORGANISM: Drosophila melanogaster

<400> SEQUENCE: 4

Met Ser Ser Ser Asp Gly Lys Leu Arg Tyr Asp Gly Arg Val Ala Val
1               5                   10                  15

Val Thr Gly Ala Gly Ala Gly Leu Gly Arg Glu Tyr Ala Leu Leu Phe
                20                  25                  30

Ala Glu Arg Gly Ala Lys Val Val Val Asn Asp Leu Gly Gly Thr His
            35                  40                  45

Ser Gly Asp Gly Ala Ser Gln Arg Ala Ala Asp Ile Val Val Asp Glu
    50                  55                  60

Ile Arg Lys Ala Gly Gly Glu Ala Val Ala Asp Tyr Asn Ser Val Ile
65                  70                  75                  80

Asp Gly Ala Lys Val Ile Glu Thr Ala Ile Lys Ala Phe Gly Arg Val
                85                  90                  95

Asp Ile Leu Val Asn Asn Ala Gly Ile Leu Arg Asp Arg Ser Leu Val
            100                 105                 110
```

Lys Thr Ser Glu Gln Asp Trp Asn Leu Val Asn Asp Val His Leu Lys
            115                 120                 125

Gly Ser Phe Lys Cys Thr Gln Ala Ala Phe Pro Tyr Met Lys Lys Gln
    130                 135                 140

Asn Tyr Gly Arg Ile Ile Met Thr Ser Ser Asn Ser Gly Ile Tyr Gly
145                 150                 155                 160

Asn Phe Gly Gln Val Asn Tyr Thr Ala Ala Lys Met Gly Leu Ile Gly
                165                 170                 175

Leu Ala Asn Thr Val Ala Ile Glu Gly Ala Arg Asn Asn Val Leu Cys
            180                 185                 190

Asn Val Ile Val Pro Thr Ala Ala Ser Arg Met Thr Glu Gly Ile Leu
        195                 200                 205

Pro Asp Ile Leu Phe Asn Glu Leu Lys Pro Lys Leu Ile Ala Pro Val
    210                 215                 220

Val Ala Tyr Leu Cys His Glu Ser Cys Glu Asp Asn Gly Ser Tyr Ile
225                 230                 235                 240

Glu Ser Ala Ala Gly Trp Ala Thr Lys Leu His Met Val Arg Gly Lys
                245                 250                 255

Gly Ala Val Leu Arg Pro Ser Leu Asp Asp Pro Val Thr Ile Glu Tyr
            260                 265                 270

Val Lys Asp Val Trp Ser Asn Val Thr Asp Met Ser Lys Ala Lys His
        275                 280                 285

Leu Gly Ala Ile Ala Glu Ala Ser Gly Thr Leu Leu Glu Val Leu Glu
    290                 295                 300

Lys Leu Lys Glu Gly Gly Gly Asp Ala Ile Glu Asp Ala Phe Glu Phe
305                 310                 315                 320

Asn Ser Lys Glu Leu Ile Thr Tyr Ala Leu Gly Ile Gly Ala Ser Val
                325                 330                 335

Lys Asn Ala Lys Asp Met Arg Phe Leu Tyr Glu Asn Asp Ala Asp Phe
            340                 345                 350

Ala Ala Ile Pro Thr Phe Phe Val Leu Pro Gly Leu Leu Leu Gln Met
        355                 360                 365

Ser Thr Asp Lys Leu Leu Ser Lys Ala Leu Pro Asn Ser Gln Val Asp
    370                 375                 380

Phe Ser Asn Ile Leu His Gly Glu Gln Tyr Leu Glu Ile Val Asp Asp
385                 390                 395                 400

Leu Pro Thr Ser Gly Thr Leu Leu Thr Asn Gly Lys Val Phe Asp Val
                405                 410                 415

Met Asp Lys Gly Ser Gly Ala Val Val Val Thr Asn Ser Glu Ser Phe
            420                 425                 430

Asp Glu Ser Gly Arg Leu Leu Val Arg Asn Gln Ser Thr Thr Phe Ile
        435                 440                 445

Val Gly Ala Gly Lys Phe Gly Gly Lys Lys Asp Pro Ile Ala Gly Val
    450                 455                 460

Val Pro Leu Gln Pro Ala Pro Asn Arg Gln Pro Asp Ala Thr Val Gln
465                 470                 475                 480

Tyr Thr Thr Ser Glu Asp Gln Ala Ala Leu Tyr Arg Leu Ser Gly Asp
                485                 490                 495

Lys Asn Pro Leu His Ile Asp Pro Gln Met Ala Leu Leu Ala Gly Phe
            500                 505                 510

Lys Thr Pro Ile Leu His Gly Leu Cys Thr Leu Gly Phe Ser Val Arg
        515                 520                 525

```
Ala Val Leu Ala Gln Phe Ala Asp Asn Asn Pro Ala Leu Phe Lys Ala
        530                 535                 540

Val Lys Val Arg Phe Ser Gly Pro Val Ile Pro Gly Gln Thr Leu Arg
545                 550                 555                 560

Val Asp Leu Trp Lys Gln Gly Thr Arg Ile Asn Phe Arg Thr Val Val
                565                 570                 575

Val Glu Thr Gly Lys Glu Val Ile Ser Gly Ala Tyr Val Asp Leu Lys
                580                 585                 590

Ser Ser Gln Ala Lys Leu
        595

<210> SEQ ID NO 5
<211> LENGTH: 453
<212> TYPE: PRT
<213> ORGANISM: Streptomyces cinnamonensis

<400> SEQUENCE: 5

Met Lys Glu Ile Leu Asp Ala Ile Gln Ala Gln Thr Ala Thr Ala Ser
1               5                   10                  15

Gly Thr Ala Ala Val Thr Ser Ala Asp Phe Ala Leu Pro Leu Pro
            20                  25                  30

Asp Ser Tyr Arg Ala Ile Thr Val His Lys Asp Glu Thr Glu Met Phe
        35                  40                  45

Ala Gly Leu Glu Ser Arg Asp Lys Asp Pro Arg Lys Ser Leu His Leu
    50                  55                  60

Asp Asp Val Pro Ile Pro Glu Leu Gly Pro Gly Glu Ala Leu Val Ala
65                  70                  75                  80

Val Met Ala Ser Ser Val Asn Tyr Asn Ser Val Trp Thr Ser Ile Phe
                85                  90                  95

Glu Pro Val Ser Thr Phe Ser Phe Leu Glu Arg Tyr Gly Arg Leu Ser
            100                 105                 110

Asp Leu Ser Lys Arg His Asp Leu Pro Tyr His Ile Ile Gly Ser Asp
        115                 120                 125

Leu Ala Gly Val Val Leu Arg Thr Gly Pro Gly Val Asn Ala Trp Asn
    130                 135                 140

Pro Gly Asp Glu Val Val Ala His Cys Leu Ser Val Glu Leu Glu Ser
145                 150                 155                 160

Ser Asp Gly His Asn Asp Thr Met Leu Asp Pro Glu Gln Arg Ile Trp
                165                 170                 175

Gly Phe Glu Thr Asn Phe Gly Gly Leu Ala Glu Ile Ala Leu Val Lys
            180                 185                 190

Ser Asn Gln Leu Met Pro Lys Pro Gly His Leu Ser Trp Glu Glu Ala
        195                 200                 205

Ala Ser Pro Gly Leu Val Asn Ser Thr Ala Tyr Arg Gln Leu Val Ser
    210                 215                 220

Arg Asn Gly Ala Gly Met Lys Gln Gly Asp Asn Val Leu Ile Trp Gly
225                 230                 235                 240

Ala Ser Gly Gly Leu Gly Ser Tyr Ala Thr Gln Phe Ala Leu Ala Gly
                245                 250                 255

Gly Ala Asn Pro Ile Cys Val Ser Ser Pro Gln Lys Ala Glu Ile
            260                 265                 270

Cys Arg Ala Met Gly Ala Glu Ala Ile Ile Asp Arg Asn Ala Glu Gly
        275                 280                 285

Tyr Lys Phe Trp Lys Asp Glu Gln Thr Gln Asp Pro Lys Glu Trp Lys
    290                 295                 300
```

```
Arg Phe Gly Lys Arg Ile Arg Glu Leu Thr Gly Gly Glu Asp Ile Asp
305                 310                 315                 320

Ile Val Phe Glu His Pro Gly Arg Glu Thr Phe Gly Ala Ser Val Tyr
                325                 330                 335

Val Thr Arg Lys Gly Thr Ile Thr Thr Cys Ala Ser Thr Ser Gly
            340                 345                 350

Tyr Met His Glu Tyr Asp Asn Arg Tyr Leu Trp Met Ser Leu Lys Arg
                355                 360                 365

Ile Ile Gly Ser His Phe Ala Asn Tyr Arg Glu Ala Trp Glu Ala Asn
370                 375                 380

Arg Leu Ile Ala Lys Gly Lys Ile His Pro Thr Leu Ser Lys Thr Tyr
385                 390                 395                 400

Arg Leu Glu Asp Thr Gly Gln Ala Ala Tyr Asp Val His Arg Asn Leu
                405                 410                 415

His Gln Gly Lys Val Gly Val Leu Ala Leu Ala Pro Glu Glu Gly Leu
                420                 425                 430

Gly Val Arg Asp Pro Glu Lys Arg Ala Gln His Ile Asp Ala Ile Asn
            435                 440                 445

Arg Phe Arg Asn Val
        450

<210> SEQ ID NO 6
<211> LENGTH: 299
<212> TYPE: PRT
<213> ORGANISM: Mus musculus

<400> SEQUENCE: 6

Met Ala Lys Cys Leu Leu Thr Ser Ser Leu Ser Val Arg Thr Lys Leu
1               5                   10                  15

Leu Gln Thr Gly Val Ser Leu Tyr Asn Thr Ser His Gly Phe His Glu
            20                  25                  30

Glu Glu Val Lys Lys Ile Leu Glu Gln Phe Pro Gly Gly Ser Ile Asp
        35                  40                  45

Leu Leu Lys Lys Gln Asn Gly Ile Gly Ile Leu Thr Leu Asn Asn Pro
50                  55                  60

Asn Lys Met Asn Ala Phe Ser Gly Val Met Met Gln Leu Leu Glu
65                  70                  75                  80

Arg Val Ile Glu Leu Glu Asn Trp Thr Glu Gly Lys Gly Leu Ile Ile
                85                  90                  95

His Gly Ala Lys Asn Thr Phe Cys Ser Gly Ser Asp Leu Asn Ala Val
                100                 105                 110

Lys Ala Leu Ser Thr Pro Glu Ser Gly Val Ala Leu Ser Met Phe Met
            115                 120                 125

Gln Asn Thr Leu Thr Arg Phe Met Arg Leu Pro Leu Ile Ser Val Ala
        130                 135                 140

Leu Val Gln Gly Trp Ala Met Gly Gly Gly Ala Glu Leu Thr Thr Ala
145                 150                 155                 160

Cys Asp Phe Arg Leu Met Thr Glu Glu Ser Val Ile Arg Phe Val His
                165                 170                 175

Lys Glu Met Gly Ile Val Pro Ser Trp Gly Gly Thr Ser Arg Leu Val
                180                 185                 190

Glu Ile Ile Gly Ser Arg Gln Ala Leu Lys Val Leu Ser Gly Thr Leu
            195                 200                 205

Lys Leu Asp Ser Lys Glu Ala Leu Asn Ile Gly Leu Thr Asp Glu Val
```

```
                210                 215                 220
Leu Gln Pro Ser Asp Glu Thr Thr Ala Leu Glu Gln Ala Gln Glu Trp
225                 230                 235                 240

Leu Glu Lys Phe Val Ser Gly Pro Pro Gln Val Ile Arg Gly Leu Lys
                245                 250                 255

Lys Ser Val Cys Ser Ala Arg Glu Leu Tyr Ile Glu Glu Ala Leu Gln
                260                 265                 270

Asn Glu Arg Asp Val Leu Glu Thr Leu Trp Gly Gly Pro Ala Asn Leu
            275                 280                 285

Glu Ala Ile Ala Lys Lys Gly Lys His Thr Lys
        290                 295

<210> SEQ ID NO 7
<211> LENGTH: 900
<212> TYPE: DNA
<213> ORGANISM: artificial
<220> FEATURE:
<223> OTHER INFORMATION: emd gene

<400> SEQUENCE: 7
atggccaagt gcctgctgac gtccagcctg agcgtgcgga ccaagctgct ccagaccggc    60
gtgtcgctgt acaacacgtc gcatgggttc acgaggagg aggtcaagaa gatcctggag    120
cagtttccgg gcggctcgat cgacctgctg aagaagcaga acggcatcgg catcctcacg    180
ctgaacaacc cgaacaagat gaacgcgttc tccggggtga tgatgctcca gctgctggag    240
cgcgtgatcg aactggagaa ctggaccgaa ggcaaaggcc tcatcatcca tggcgcgaag    300
aacaccttct gctcggggtc ggacctgaat gccgtgaaag ccctgagcac gccggaatcg    360
ggcgtggcgc tgagcatgtt catgcagaac ccctgaccc gcttcatgcg gctgccgctg    420
atctcggtcg cactggtgca aggctgggcc atgggcggcg cgccgaact gacgaccgcg    480 tgcgactttc gcctgatgac ggaggagtcg gtcattcgct cgtgcacaa ggagatgggc    540 atcgtcccgt cgtggggcgg cacctcccgc ctggtggaga tcatcggcag ccgccaagcg    600
ctgaaggtcc tgagcggcac cctgaagctg gactcgaagg aggccctgaa catcggcctg    660
accgatgagg tgctccagcc gtcggacgaa accaccgccc tggaacaggc ccaggaatgg    720
ctggagaagt tcgtgagcgg cccgccccag gtcattcgcg gcctgaagaa gtccgtgtgc    780
agcgcacgcg agctgtatat cgaggaggcg ctccagaatg aacgcgatgt gctgaaaacg    840
ctgtggggcg gccccgccaa tctggaagcc atcgcgaaga agggcaagca caccaagtag    900

<210> SEQ ID NO 8
<211> LENGTH: 261
<212> TYPE: DNA
<213> ORGANISM: artificial
<220> FEATURE:
<223> OTHER INFORMATION: Poe1

<400> SEQUENCE: 8
tcagaaaatt atttaaatt tcctcttgac aggccggaat aactcccata taatgcgcca    60
ccactgattg acaattaatc atcgaattag tataatagta cgcaagttct tgacactgta    120
gcgggaaggc gttataatgc acaccccgcg cttgacagcg cgtgcgttgc aaggtataat    180
ggactcaaat gtcttgacac tttatgcttc cggctctata atgtgtggaa ttgtgagcgg    240
ataacaattt cacacaggaa a                                              261

<210> SEQ ID NO 9
```

<211> LENGTH: 2786
<212> TYPE: DNA
<213> ORGANISM: Yarrowia lipolytica

<400> SEQUENCE: 9

```
aggaaacaat tgcacgtgca gagagacaat caaatcatgt ctggagaact aagatacgac      60
ggaaaggtcg tcattgttac cggtgccggt ggcggtctcg gtaaggcata cgcccttttc     120
tacggctctc gaggagcctc tgttgttgtc aacgatcttg gtggcgactt caagggcgac     180
ggtgcccagg ctggcagtgg caagcgagtt gccgatgttg tcgtcgacga gattgtttcc     240
aagggaggca aggctgttgc taactacgac tctgtcgaga acggtgacaa gattgtcgag     300
actgccgtca aggcttttgg ctccgtccac attgtcatca caacgccgg tattctccga      360
gatatttcct tcaagaagat gaccgacaag gactgggatc ttgtctacaa ggtccacgtt     420
ttcggtgcct acaaggttac ccgagctgcc tggccttact tccgaaagca gaagtacggt     480
cgagttatct ctacctcttc cgctgctggt ctttacggaa acttcggcca gaccaactac     540
tccgctgcca agctcgccct ggttggtttc ggtgagactc tcgccaagga gggtgccaag     600
tacaacatta cttccaacgt catcgctcct cttgctgctt cccgaatgac cgagacagtc     660
atgcccgagg atatcctcaa gctcctcaag cctgagtacg ttgttcctct ggtcggctac     720
ctcacccacg actctgtcac cgagtcttat ggtatttacg aggtcggtgc tggttacatg     780
gctaaaatcc gatgggagcg aggcaacggt gctgttttca agggcgacga cactttcacc     840
ccgtctgcta ttctgaagcg atgggatgag gtcacctctt ttgagagccc cacctaccct     900
aacggccctc tgacttcttc caaatacgct gaggagtctg ttaagcgacc cgagaacccc     960
cagggaccca ccgtctcctt caaggaccag gttgtcattg tcactggagc cggtgctggc    1020
attggccgag cttactctca cctccttgct aagcttggtg ccaaggtcgt tgttaacgat    1080
ttcggtaacc ctcagaaggt tgtcgatgaa attaaggccc tcggtggtat cgccgtcgct    1140
gacaagaaca acgtcatcca cggtgagaag gttgttcaga ccgctatcga cgccttcggt    1200
gctgtccacg ccgttgtcaa caacgctggt attctccgag acaagtcttt cgccaacatg    1260
gatgatgaga tgtggcagct gatctttgat gtccacctca acggtactta ctccgttacc    1320
aaggccgcgt ggcccactt ccttaagcag aagtacggcc gtgtcatcaa caccacctca    1380
acttctggta tctacggtaa cttcggccag gccaactact ctgccgccaa ggctggtatc    1440
ctcggtttct cccgagctct tgctcgagag ggtgagaagt acaacattct tgtcaacacc    1500
attgcccta cgctggtac tgccatgact gcttctgtct tcactgagga gatgctcgag    1560
ctcttcaagc ccgatttcat cgcacccatc accgtcctgc ttgcttccga tcaggctccc    1620
gtcaccggtg atctgtttga gactggttct gcttggatcg gacagactcg atggcagcga    1680
gctggtggta aggccttcaa caccaagaag ggtgtcaccc ccgaaatggt tcgagacagc    1740
tgggctaaga tcgtcgactt cgatgatggt aactccaccc atcccaccac tccctccgag    1800
tctactactc agattcttga gaacatcttc aacgtgcctg atgaggaggt tgaggagact    1860
gctctcgttg ctggtcccgg tggtcccggt atcctcaaca aggagggcga acctttcgac    1920
tacacttaca cttaccgaga cctcattctt tacaaccttg gtctcggtgc caaggctaat    1980
gagctcaagt atgtcttcga gggtgatgat gacttccaga ccgtgcccac tttcggtgtt    2040
atcccttaca tgggtggcct catcactacc aactatggcg acttcgttcc taacttcaac    2100
cctatgatgc ttctccacgg tgagcagtac cttgaaatcc gacagtggcc tattcctacc    2160
aatgctacat tggagaacaa ggctaaggtc atcgatgtcg ttgacaaggg caaggctgcc    2220
```

```
ctccttgtca ctgctaccac caccacgaac aaggagactg gtgaggaggt tttctacaac      2280
gagtcttctc tcttcatccg aggctctggt ggtttcggtg gtaagtctac cggtactgac      2340
cgtggcgctg ccactgctgc caacaagccc ctgctcgag ctcctgactt cgttaaggag       2400
atcaagatcc aggaggacca ggctgccatt taccgactt ctggtgatta caaccctctt       2460
cacatcgacc ctgcttttgc tgctgttggt aactttgacc gacctattct ccacggtctc      2520
tgctcttttg gtgtctccgg taaggctctt tacgatcagt ttggtccttt caagaacgct      2580
aaggtccgat tgctggtca cgtcttccct ggtgagaccc tgaaggttga gggctggaag       2640
gagggcaaca aggtcatttt ccagaccaag gttgttgagc gaggtactac cgccatcagc      2700
aatgccgcca ttgagctctt ccccaaggat gctaagctct aacctgccgg cctggttcaa      2760
ccagtcggca gccgactagt ggatcc                                           2786

<210> SEQ ID NO 10
<211> LENGTH: 248
<212> TYPE: DNA
<213> ORGANISM: Escherichia coli

<400> SEQUENCE: 10
gcgcgcgaat tctgcttctg gcgtcaggca gccatcggaa gctgtggtat ggctgtgcag       60
gtcgtaaatc actgcataat tcgtgtcgct caaggcgcac tcccgttctg gataatgttt      120
tttgcgccga catcataacg gttctggcaa atattctgaa atgagctgtt gacaattaat      180
catccggctc gtataatgtg tggaattgtg agcggataac aatttcacac aggaaacaat      240
tggcgcgc                                                              248

<210> SEQ ID NO 11
<211> LENGTH: 438
<212> TYPE: DNA
<213> ORGANISM: Cupriavidus necator

<400> SEQUENCE: 11
ctatccattt aaatcctggc gtggttcgtg ttcggcaact acgccgatcc ggccacgggg       60
gcggcggtat cgggcgacct gcaccgctac tttgccggcg accccggcgc aggcctgttc      120
atgaccggct ttttcccggt gatgatgttc ggcctgcccg cggcctgcct ggcgatgtac      180
cacgagacgc cgccggcgcg gcgcgcgctg gttggccgca tgctgttctc gatggcactg      240
acctcgttcc tgaccggcat caccgagccg atcgagttca gcttcatgtt cctggcgccg      300
gtgctgtacg gcctgcatgc gctgatgacc ggcctgtcga tggcgctgtg ccatgcgctc      360
gatatccggc tgggcttcac cttctcggcc ggcgcgatcg actatgtgct gggctacggg      420
ctgtatttaa atccgaat                                                    438

<210> SEQ ID NO 12
<211> LENGTH: 828
<212> TYPE: DNA
<213> ORGANISM: Cupriavidus necator

<400> SEQUENCE: 12
ctatccattt aaattcagcc attttgcttc cagaagtcgc ggcggccggt gcagaaatgc       60
gacggcgcca gggtcaggcg aaagatagac ggcaaccgac aataaaaata ccagtgaaaa      120
ccactacaac aatattgtat ctaagtggca tctttattga ggcaaggcaa acagtccttt      180
ggatggtcct cacattcgcc ttaatcacca taacccacgg agataggtaa gattttttcca     240
```

```
aatcacagca gcattttccg acgccataat cagcagaacc atttcaatac caattgacgt    300
aaagcgaagc gatggcgatg ttatcgccca gatgacgcaa tgccgcacca tcgacgtcaa    360
atgtcctaaa gtggtatcat cacctccaca ctctggtacc tacgaggatt cgcatgcccg    420
gcacgcccgg caaccggcgg ctcgaccggg ggcggggtcg gatcttcctc tggcggcaac    480
ggcaagtccg gggggatgcc cggcggcccg ggctcttcga ccggggggcac ggtatggcgc    540 ggctgcaggc gcgcaccggc gtgggggttc ggcaaggcgg gcatgcgggg tctccgtggc    600
cgggtttcct cctcattgaa gcaaacccgg ccggtgcgcg ccagtattga tgcagacgcc    660
gctcaggcgt gttgccggcg cacgaagaac agccgcgcgc ccaccgccat cagcacgctg    720
ccaaagaagc ggttctgcca gcgcaccgcg cgcgcattac ggaacagccc ctgcatgcgc    780
gacgccagca gcgcatagcc atgcatcacc accaatttaa atccgaat              828
```

```
<210> SEQ ID NO 13
<211> LENGTH: 907
<212> TYPE: DNA
<213> ORGANISM: Cupriavidus necator

<400> SEQUENCE: 13
gcgcgcattt aaatgggaca gcagcaggat ttccgcacgc gccgcggcgt cgtccggcgg     60
caccagcact tcttcgaatt ccaggccggc aaagcgcgcc agcagccagc cgcgcagcga    120
ccatgaggaa taggtcttgc tgctaatggt gagtgtggtc ttggacatcg cgcctccttt    180
actgcttgtt gccgctaatg ccgcgcacc tatgcagtgc atccggcagg caccagtctg    240
aagccgctgc gcgcaacgcg ccgcgaagcg gcgccatgcc catgcgccag gcgcatgcct    300
cgctacttgc gcggcattgt ccgcccgctc acagcacaat gcgcaaggcg cgtgccaggc    360
ataaactgat ggccaattgg cgcgcactag tcccggcagc cgccagcgcg ctggcctcgc    420
ttatcatggc agctgcgccg ggcggcacgc gaacggcgcg gcaccaacga tcaacatgcc    480
attgctaccg acacaagact tccagggcca gccgctggtc cggatcggcg atgccgacac    540
gttcctgctg ctcgccccgc aacacggcgg gcggctggtc cgctgggtgc accgcggaca    600
ggacatcctc tactggccgg acgctgccga ctggtcccgc ccggccaagg tccgcggcgg    660
caacccgctg ctgtttccgt ttatcggccg gcattttgcc gatggcaatc cgggccagtg    720
gcgcgacgga caaggaccca tgcgcacgct ggcgcagcac ggctttgcgc gcgacctgcc    780
cttcgacgtc agcgccatcg acgcgcaagc cgcgatcacg atgacgctgc gcgacagcga    840
tgcaacgcgg gccggctacc cctttgcctt tgtcttcgac gccatctacc gctatttaaa    900
tgcgcgc                                                            907
```

```
<210> SEQ ID NO 14
<211> LENGTH: 2693
<212> TYPE: DNA
<213> ORGANISM: artificial
<220> FEATURE:
<223> OTHER INFORMATION: Poe1-ccr-emd

<400> SEQUENCE: 14
gcgcgcgaat tctcagaaaa ttattttaaa tttcctcttg acaggccgga ataactccca     60
tataatgcgc caccactgat tgacaattaa tcatcgaatt agtataatag tacgcaagtt    120
cttgacactg tagcgggaag gcgttataat gcacacccccg cgcttgacag cgcgtgcgtt    180
gcaaggtata atggactcaa atgtcttgac actttatgct tccggctcta taatgtgtgg    240
aattgtgagc ggataacaat ttcacacagg aaacaattgc acgtgcagag agacaatcaa    300
```

```
atcatgaagg aaatcctgga cgcgattcag gcccagaccg cgaccgcgag cggcaccgcc    360
gcggtcacgt ccgccgactt cgccgctctc cccctgcccg actcgtaccg cgcgatcacc    420
gtgcacaagg acgagacgga gatgttcgcg ggcctcgagt cccgtgacaa ggaccccgc     480 aagtcgctcc atctggacga cgtgccgatc cccgaactcg gccccggtga ggccttggtg    540
gccgtcatgg cctcctcggt caactacaac tccgtgtgga cctcgatctt cgagcccgtc    600
tccaccttca gcttcctgga gcggtacggc cggctcagcg acctgagcaa cgccacgac     660 ctgccgtacc acatcatcgg ctccgacctg gcgggcgtcg tgctgcgcac cgggcccggc    720
gtgaacgcct ggaacccggg cgacgaggtc gtcgcgcact gcctgagcgt cgagctggag    780
tcctccgacg gccacaacga cacgatgctc gaccccgagc agcgcatctg gggcttcgag    840
accaacttcg gcggtctcgc cgagatcgcg ctcgtcaagt ccaaccagct catgccgaag    900
cccggtcacc tgagctggga ggaggccgcc tcgcccggcc tggtgaactc caccgcgtac    960
cgccagctgg tgtcccgcaa cggcgccggc atgaagcagg cgacaacgt gctgatctgg    1020 ggcgcgagcg gcggactcgg gtcgtacgcc acgcagttcg cgctcgccgg cggcgccaac   1080
cccatctgtg tcgtctccag cccccagaag gcggagatct gccgcgcgat gggcgccgag   1140
gcgatcatcg accgcaacgc cgagggctac aagttctgga aggacgagca gacccaggac   1200
cccaaggagt ggaagcgctt cggcaagcgc atccgcgagc tcaccggcgg cgaggacatc   1260
gacatcgtct tcgagcaccc cggccgcgag accttcggcg cctcggtcta cgtcacgcgc   1320
aagggcggca ccatcaccac ctgcgcctcg acctcgggct acatgcacga gtacgacaac   1380
cgctacctgt ggatgtccct gaagcgcatc atcggctcgc acttcgccaa ctaccgcgag   1440
gcgtgggagg ccaaccgcct gatcgccaag ggcaagatcc acccgacgct ctccaagacg   1500
taccgcctgg aggacaccgg ccaggccgcc tacgacgtcc accgcaacct ccaccagggc   1560
aaggtcggcg tcctcgccct cgcgcccgag gagggcctgg gcgtgcgcga cccggagaag   1620
cgggcccagc acatcgacgc gatcaaccgt ttccgcaacg tctgacgctt gcatgagtgc   1680
cggcgtgcgt catgcacggc gccggcaggc ctgcaggttc cctcccgttt ccattgaaag   1740
gactacacaa tggccaagtg cctgctgacg tccagcctga gcgtgcggac caagctgctc   1800
cagaccggcg tgtcgctgta caacacgtcg catgggttcc acgaggagga ggtcaagaag   1860
atcctggagc agtttccggg cggctcgatc gacctgctga agaagcagaa cggcatcggc   1920
atcctcacgc tgaacaaccc gaacaagatg aacgcgttct ccggggtgat gatgctccag   1980
ctgctggagc gcgtgatcga actggagaac tggaccgaag gcaaaggcct catcatccat   2040
ggcgcgaaga acaccttctg ctcggggtcg gacctgaatg ccgtgaaagc cctgagcacg   2100
ccggaatcgg gcgtggcgct gagcatgttc atgcagaaca ccctgacccg cttcatgcgg   2160
ctgccgctga tctcggtcgc actggtgcaa ggctgggcca tgggcggcgg cgccgaactg   2220
acgaccgcgt gcgactttcg cctgatgacg gaggagtcgg tcattcgctt cgtgcacaag   2280
gagatgggca tcgtcccgtc gtggggcggc acctcccgcc tggtggagat catcggcagc   2340
cgccaagcgc tgaaggtcct gagcggcacc ctgaagctgg actcgaagga ggccctgaac   2400
atcggcctga ccgatgaggt gctccagccg tcggacgaaa ccaccgccct ggaacaggcc   2460
caggaatggc tggagaagtt cgtgagcggc ccgccccagg tcattcgcgg cctgaagaag   2520
tccgtgtgca gcgcacgcga gctgtatatc gaggaggcgc tccagaatga acgcgatgtg   2580
ctggaaacgc tgtggggcgg ccccgccaat ctggaagcca tcgcgaagaa gggcaagcac   2640
```
accaagtagc ctgccggcct ggttcaacca gtcggcagcc gactagtgcg cgc        2693

<210> SEQ ID NO 15
<211> LENGTH: 1075
<212> TYPE: DNA
<213> ORGANISM: Cupriavidus necator

<400> SEQUENCE: 15
gcgcgcattt aaatccggac cttcgtgcgg ctcaagcccc agcacgtcgc cgggcagcga      60
aaaacccgtt acctgccgcc agcccagcgg cgattcatag acctgcttgg cgctgccatg     120
gcgcagcggg tagaccgtca gcgcagggcg cccctggcga acacatgct cgccggtgcg      180
cacctctacc agctccggct gcagcgccat cggcgcgtgc ggcaggggg cttgtggccc      240
ggcattgtgg caaacgtggc gaaagaggca gagcaggcag gctggggcgc cgctgtccgg     300
catggtgtca ttgtcctccg gtgacgatgg ccaagtataa aacgccggca acgcaagcca     360
tctcgctgcg atctgcattc tttcgtatgg ctggtttaaa aatttcgcat tacggggcg      420
aggctcgttg cgtttgtgcc ataagcgcgg gagcacgccg gcgggcgtaa tgcggattgt     480
gatatgctgc aacgcaacaa taaaggcata ggaggagatc gcgtcacacg atcaggagtc     540
ctccaattga tcgatactag tagtcgggca gcaccaatgc gcatcaagcg cgcacaagta     600
aagggagggc gcctgccctc ccttttcct tgcagcagcc gcgtcagcc gcgagcggt        660
ccttgacgaa cagcgcagtc accatgccca gcacgcacg cgcgaccaca tagtgggccg      720
gtgccagcgg atcctgcttc agcatcagcg tgacgaccat cggcgtcagc ccgccgaaga     780
tcgcatacga cacgttgtac gagaatgaca ggcccgagaa gcgcacctgc gccgggaacg     840
cattgaccag cacgaacggc accgcgccga tggtgccgac caggaagccg gtcagcgcat     900
agagcggcag cagcaggtcg gggcgggtga agatcgtcgt gtagaacata taggcgcaga     960
tggccagcag caggccgccg acgaacagcg tgcggcgcgc accgatgcgg tcggctaatg    1020
cgccggagac gacacagccg atcgtcaggc acagcgtggc gatttaaatg cgcgc          1075

<210> SEQ ID NO 16
<211> LENGTH: 2426
<212> TYPE: DNA
<213> ORGANISM: artificial
<220> FEATURE:
<223> OTHER INFORMATION: ccr-emd

<400> SEQUENCE: 16
gcgcgccaat tgcacgtgca gagagacaat caaatcatga aggaaatcct ggacgcgatt      60
caggcccaga ccgcgaccgc gagcggcacc gccgcggtca cgtccgccga cttcgccgct     120
ctccccctgc ccgactcgta ccgcgcgatc accgtgcaca aggacgagac ggagatgttc     180
gcgggcctcg agtcccgtga caaggacccc cgcaagtcgc tccatctgga cgacgtgccg     240
atccccgaac tcggccccgg tgaggccttg gtgccgtca tggcctcctc ggtcaactac     300
aactccgtgt ggaccttgat cttcgagccc gtctccacct tcagcttcct ggagcggtac     360
ggccggctca gcgacctgag caagcgccac gacctgccgt accacatcat cggctccgac     420
ctggcgggcg tcgtgctgcg caccgggccc ggcgtgaacg cctggaaccc gggcgacgag     480
gtcgtcgcgc actgcctgag cgtcgagctg gagtcctccg acggccacaa cgacacgatg     540
ctcgaccccg agcagcgcat ctgggcttc gagaccaact tcggcggtct cgccgagatc      600
gcgctcgtca agtccaacca gctcatgccg aagcccggtc acctgagctg ggaggaggcc     660
gcctcgcccg gcctggtgaa ctccaccgcg taccgccagc tggtgtcccg caacggcgcc     720

```
ggcatgaagc agggcgacaa cgtgctgatc tggggcgcga gcggcggact cgggtcgtac      780
gccacgcagt tcgcgctcgc cggcggcgcc aaccccatct gtgtcgtctc cagccccag       840 aaggcggaga tctgccgcgc gatgggcgcc gaggcgatca tcgaccgcaa cgccgagggc      900
tacaagttct ggaaggacga gcagaccag gaccccaagg agtggaagcg cttcggcaag       960
cgcatccgcg agctcaccgg cggcgaggac atcgacatcg tcttcgagca ccccggccgc     1020
gagaccttcg cgcctcggt ctacgtcacg cgcaagggcg gcaccatcac cacctgcgcc      1080
tcgacctcgg gctacatgca cgagtacgac aaccgctacc tgtggatgtc cctgaagcgc     1140
atcatcggct cgcacttcgc caactaccgc gaggcgtggg aggccaaccg cctgatcgcc     1200
aagggcaaga tccacccgac gctctccaag acgtaccgcc tggaggacac cggccaggcc     1260
gcctacgacg tccaccgcaa cctccaccag ggcaaggtcg cgtcctcgc cctcgcgccc      1320 gaggagggcc tgggcgtgcg cgacccggag aagcgggccc agcacatcga cgcgatcaac     1380
cgtttccgca acgtctgacg cttgcatgag tgccggcgtg cgtcatgcac ggcgccggca     1440
ggcctgcagg ttccctcccg tttccattga aaggactaca caatggccaa gtgcctgctg     1500
acgtccagcc tgagcgtgcg gaccaagctg ctccagaccg cgtgtcgct gtacaacacg      1560 tcgcatgggt tccacgagga ggaggtcaag aagatcctgg agcagtttcc gggcggctcg     1620
atcgacctgc tgaagaagca gaacggcatc ggcatcctca cgctgaacaa cccgaacaag     1680
atgaacgcgt tctccggggt gatgatgctc cagctgctgg agcgcgtgat cgaactggag     1740
aactggaccg aaggcaaagg cctcatcatc catggcgcga agaacacctt ctgctcgggg     1800
tcggacctga atgccgtgaa agccctgagc acgccggaat cgggcgtggc gctgagcatg     1860
ttcatgcaga acaccctgac ccgcttcatg cggctgccgc tgatctcggt cgcactggtg     1920
caaggctggg ccatgggcgg cggcgccgaa ctgacgaccg cgtgcgactt cgcctgatg      1980 acggaggagt cggtcattcg cttcgtgcac aaggagatgg gcatcgtccc gtcgtggggc     2040
ggcacctccc gcctggtgga gatcatcggc agccgccaag cgctgaaggt cctgagcggc     2100
accctgaagc tggactcgaa ggaggccctg aacatcggcc tgaccgatga ggtgctccag     2160
ccgtcggacg aaaccaccgc cctggaacag gcccaggaat ggctggagaa gttcgtgagc     2220
ggcccgcccc aggtcattcg cggcctgaag aagtccgtgt gcagcgcacg cgagctgtat     2280
atcgaggagg cgctccagaa tgaacgcgat gtgctggaaa cgctgtgggg cggccccgcc     2340
aatctggaag ccatcgcgaa gaagggcaag cacaccaagt agcctgccgg cctggttcaa     2400
ccagtcggca gccgactagt gcgcgc                                          2426

<210> SEQ ID NO 17
<211> LENGTH: 248
<212> TYPE: DNA
<213> ORGANISM: Escherichia coli

<400> SEQUENCE: 17
gcgcgccaat tgtgcttctg cgtcaggca gccatcggaa gctgtggtat ggctgtgcag       60
gtcgtaaatc actgcataat tcgtgtcgct caaggcgcac tcccgttctg gataatgttt     120
tttgcgccga catcataacg gttctggcaa atattctgaa atgagctgtt gacaattaat     180
catccggctc gtataatgtg tggaattgtg agcggataac aatttcacac aggaaacaat     240
tggcgcgc                                                             248
```